US008129525B2

(12) United States Patent
Pitner et al.

(10) Patent No.: US 8,129,525 B2
(45) Date of Patent: Mar. 6, 2012

(54) LONG WAVELENGTH THIOL-REACTIVE FLUOROPHORES

(75) Inventors: J. Bruce Pitner, Durham, NC (US); Douglas B. Sherman, Durham, NC (US); Arounaguiry Ambroise, Morrisville, NC (US); Joseph Thomas, Raleigh, NC (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 179 days.

(21) Appl. No.: 12/489,121

(22) Filed: Jun. 22, 2009

(65) Prior Publication Data

US 2010/0003763 A1 Jan. 7, 2010

Related U.S. Application Data

(62) Division of application No. 11/131,283, filed on May 18, 2005, now Pat. No. 7,563,891.

(60) Provisional application No. 60/573,944, filed on May 21, 2004, provisional application No. 60/599,514, filed on Aug. 6, 2004.

(51) Int. Cl.
*C07D 413/06* (2006.01)
(52) U.S. Cl. ........................ 544/99; 544/105; 514/230.5
(58) Field of Classification Search ...................... 544/99
See application file for complete search history.

(56) References Cited

U.S. PATENT DOCUMENTS

| | | | |
|---|---|---|---|
| 3,891,669 A | 6/1975 | Kanaoka et al. |
| 4,507,480 A | 3/1985 | Horgan et al. |
| 5,631,169 A | 5/1997 | Lakowicz et al. |
| 5,696,157 A | 12/1997 | Wang et al. |
| 5,965,746 A | 10/1999 | Fujita et al. |
| 6,197,534 B1 | 3/2001 | Lakowicz et al. |
| 6,214,628 B1 | 4/2001 | Lakowicz et al. |
| 6,277,627 B1 | 8/2001 | Hellinga |
| 6,395,556 B1 | 5/2002 | Lakowicz et al. |
| 6,521,446 B2 | 2/2003 | Hellinga |
| 6,538,129 B1 | 3/2003 | Terpetschnig et al. |
| 6,605,459 B2 | 8/2003 | Rice et al. |
| 6,663,846 B1 | 12/2003 | McCombs et al. |
| 6,855,556 B2 | 2/2005 | Amiss et al. |
| 2002/0004217 A1 | 1/2002 | Hellinga |
| 2002/0045268 A1 | 4/2002 | Lakowicz et al. |
| 2003/0129622 A1 | 7/2003 | Hellinga et al. |
| 2003/0134346 A1 | 7/2003 | Amiss et al. |
| 2003/0153026 A1 | 8/2003 | Alarcon et al. |
| 2003/0228682 A1 | 12/2003 | Lakowicz et al. |
| 2004/0039158 A1 | 2/2004 | Lakowicz |
| 2004/0087842 A1 | 5/2004 | Lakowicz et al. |
| 2004/0118681 A1 | 6/2004 | Hellinga et al. |
| 2004/0234962 A1 | 11/2004 | Alarcon et al. |
| 2005/0014290 A1 | 1/2005 | Hsieh et al. |
| 2005/0042662 A1 | 2/2005 | Li et al. |
| 2005/0042704 A1 | 2/2005 | Alarcon et al. |

FOREIGN PATENT DOCUMENTS

| | | |
|---|---|---|
| DE | 19937024 | 2/2001 |
| GB | 2319250 | 5/1998 |
| JP | 60 169453 | 9/1985 |
| JP | 60 228448 | 11/1985 |
| WO | WO 97/29154 A1 | 8/1997 |
| WO | WO 97/40104 | 10/1997 |
| WO | WO 00/03727 | 1/2000 |
| WO | WO 00/58405 | 10/2000 |
| WO | WO 01/11370 | 2/2001 |
| WO | WO 2004/101769 | 11/2004 |

OTHER PUBLICATIONS

Database Accession No. 002559643, Sep. 10, 1982.
Database Accession No. 002559644, Apr. 2, 1983.
Boos, et al., "Transport Properties of the Galactose-Binding Protein of *Escherichia coli*. Occurrence of two Conformational States," *J. Biol. Chem.*, 1971, pp. 621-628, vol. 246.
Boos, et al., "Transport Properties of the Galactose-Binding Protein of *Escherichia coli*. Substrate-Induced Conformational Change," *J. Biol. Chem.*, 1971, pp. 917-924, vol. 247.
Cornelissen-Gude, et al., "Photophysical Properties of Squaraine Derivatives: Evidence for Charge Separation," *Journal of Physical Chemistry A*, 1997, pp. 9673-9677, vol. 101.
Das, et al., "Photochemistry of Squaraine Dyes. 8. Photophysical Properties of Crown Ether Squaraine Fluoroionophores and Their Metal Ion Complexes," *J. Phys. Chem.*, 1994, pp. 9291-9296, vol. 98.
Dattelbaum, et al., Optical Determination of Glutamine Using a Genetically Engineered Protein, *Analytical Biochemistry*, 2001, pp. 89-95, vol. 291.
D'Auria, et al., "A Novel Fluorescence Competitive Assay for Glucose Determinations by Using a Thermostable Glucokinase From the Thermophillic Microorganism *Bacillus stearothermophilus*," *Anal. Biochem.*, 2002, pp. 138-144, vol. 303.

(Continued)

*Primary Examiner* — Kahsay T Habte
(74) *Attorney, Agent, or Firm* — Alston & Bird LLP

(57) ABSTRACT

Reactive fluorescent dyes compositions and methods of using same are disclosed. Nile Red nucleus dyes are disclosed having thiol-reactive groups. Nile Red nucleus dyes are disclosed that exhibit a fluorescence emission of at least about 575 nm. The Nile Red nucleus dyes are of the following formulae:

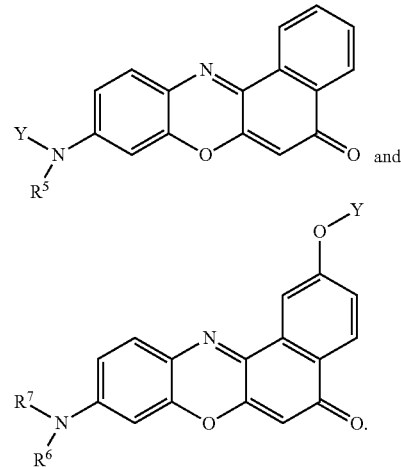

7 Claims, 7 Drawing Sheets

OTHER PUBLICATIONS

De Lorimier, et al., "Construction of a Fluorescent Biosensor Family," *Protein Science*, 2002, pp. 2655-2675, vol. 11.

Griffiths, et al., "The Influence of Chain-Length and Electron-Acceptor Residues in 3-Substituted 7-N, N-Diethylaminocoumarin Dyes," *Dyes and Pigments*, 1995, pp. 327-339, vol. 28.

Gruber, et al., Preparation of Thiol-Reactive Cy5 Derivatives from Commercial Cy5 Succinimidyl Ester, *Bioconjug Chem.*, 2000, pp. 161-166, vol. 11.

Hirshberg, et al., Crystal Structure of Phosphate Binding Protein Labeled With a Coumarin Fluorophore, A Probe for Inorganic Phosphate, *Biochemistry*, 1998, pp. 10381-10385, vol. 37.

Hossain, et al., "Utility of Intensely Fluorescent Cyanine Dyes (Cy3) for Assay of Gap Junctional Communication by Dye-Transfer," *Neuroscience Letters*, 1995, pp. 71-74, vol. 184.

Kukrer, et al., Red to Near IR Fluorescent Signaling of Carbohydrates, *Tetrahedron Lett.*, 1999, pp. 9125-9128, vol. 40.

Le Bris, "Synthesis and Properties of Some 7-Dimethylamino-1, 4-Benzoxazin-2-Ones," *J. Heterocycl. Chem.*, 1985, pp. 1275-1280, vol. 22.

Long, et al., "Synthesis and Fluorescence Properties of Novel Benzo[a] Phenoxazin-5-One Derivatives," *J. Heterocycl. Chem.*, 1999, pp. 895-899, vol. 36.

Mishra, et al., "Cyanines During the 1990s: A Review," *Chem. Rev.*, 2000, pp. 1973-2012, vol. 100.

Mowbray, et al., "Structure of the Periplasmic Glucose/Galactose Receptor of *Salmonella typhimurium*," *Recetpor*, 1990-1991, pp. 41-53, vol. 1.

Pisarchick, et al., "Binding of a Monoclonal Antibody and its FAb Fragment to Supported Phospholipid Monolayers Measured by Total Internal Reflection Fluorescence Microscopy," *Biophys. J.*, 1990, pp. 1235-1249, vol. 58.

Pitner, et al., Design and Synthesis of a Squaraine Dye for Long Wavelength Fluorescence-Based Biosensors, in Genetically Engineered and Optical Probes for Biomedical Applications III, edited by D.J. Bornhip, S.I. Achilefu, R. Raghavachari, A.P. Savitsky, Proceedings of *SPIE*, 2005, pp. 24-29, vol. 5704.

Pitner, et al., Design and Synthesis of a Squaraine Dye for Long Wavelength Fluorescence-Based Biosensors, Poster Presented at the 56th Southeastern Regional Meeting of the American Chemical Society, 2004 pp. 1-3.

Salins, et al., A Novel Reagentless Sensing System for Measuring Glucose Based on the Galactose/Glucose-Binding Protein, *Anal. Biochem.*, 2001, pp. 19-26, vol. 294.

Schauer-Vukasinovic, et al., "Rational Design of a Calcium Sensing System Based on Induced Conformational Changes of Calmodulin," *J. Am. Chem.. Soc.*, 1997, pp. 11102-11103, vol. 119.

Sharma, et al., "Development of a Reagentless Biosensing System for Glucose," *Abstracts of Papers of the American Chemical Society*, 2001, p. 46, vol. 221.

Sohanpal, et al., "Reagentless Fluorescence Sensors Based Upon Specific Binding-Proteins," *Sensors and Actuators B—Chemical*, 1993, pp. 547-552, vol. 11.

Soper, et al., "Steady-State and Piosecond Laser Fluorescence Studies of Nonradiative Pathways Intricarbocyanine Dyes: Implications to the Design of Near-IR Fluorochromes with Highfluorescence Efficiencies," *J. Am. Chem.. Soc.*, 1994, pp. 3744-3752, vol. 116.

Strekowski, et al., "Substitution Reactions of a Nucleofugal Group in Heptamethine Cyanine Dyes. Synthesis for an Isothiocyanato Derivative for Labeling of Proteins With a Near-Infrared Chromophore," *J. Org. Chem.*, 1992, pp. 4578-4580, vol. 57.

Terpetsching, et al., "Synthesis of Squaraine-N-Hydroxysuccinimide Ester and Their Biological Application as Long-Wavelength Fluorescent Labels," *Analytical Biochemistry*, 1994, pp. 197-204, vol. 217.

Terpetsching, et al., "Synthesis and Characterization of Unsymmetrical Squaraines: A New Class of Cyanine Dyes," *Dyes and Pigments*, 1993, pp. 227-234, vol. 21.

Terpetsching, et al., "Synthesis, Spectral Properties and Photostabilities of Symmertical and Unsymmetrical Squaraines; A New Class of Fluorophores With Long-Wavelength Excitation and Emission," *Analytica Chimica Acta*, 1993, pp. 633-641, vol. 282.

Thomas, et al., "Long Wavelength Fluorescent dyes for Biosensors," *Diabetes Technology Meeting*, Philadelphia, PA, 2004.

Tolosa, et al., "Glucose Sensor for Low-Cost Lifetime-Based Sensing Using a Genetically Engineered Protein," *Anal. Biochem.*, 1999, pp. 114-120, vol. 267.

Tolosa, et al., Optical Biosensors Based on Genetically-Engineered *E-coli* Periplasmic Binding Proteins, *Biophys. J.*, 2000, p. 2453, vol. 78.

Turcatti, et al., "Probing the Structure and Function of the Tachykinin Neurokinin-2 Receptor Through Biosynthetic Incorporation of Fluorescent Amino Acids at Specific Sites," *J. Biol. Chem.*, 1996, pp. 19991-19998, vol. 271.

Vyas, et al., Sugar and Signal-Transducer Binding Sites of the *Escherichia coli* Galactose Chemoreceptor Protein, *Science*, 1988, pp. 1290-1295, vol. 242.

Zhou, et al., "Periplasmic Binding Protein Based Biosensors 1. Preliminary Study of Maltose Binding Protein as Sensing Element for Maltose Biosensor," *Biosensors and Bioelectronics*, 1991, pp. 445-450, vol. 6.

LONG WAVELENGTH THIOL-REACTIVE FLUOROPHORES

CROSS REFERENCE TO RELATED APPLICATIONS

This application is a divisional application of U.S. Utility application Ser. No. 11/131,283, filed May 18, 2005, which claims the benefit of U.S. Provisional Application Ser. No. 60/573,944, filed May 21, 2004 and U.S. Provisional Application Ser. No. 60/599,514, filed Aug. 6, 2004, the contents of which are herein incorporated by reference in their entirety.

This application is based on research work that was funded in part by a grant from the U.S. Army Medical Research and Material Command (USAMRMC) under TMM Contract No. W81XWH-04-1-0076 so that the United States government may have certain rights in this invention.

FIELD OF THE INVENTION

The embodiments of the present invention are directed to novel long wavelength fluorophores for use in the detection of an analyte. Additional embodiments are directed to fluorophores that contain a thiol-reactive site that can be covalently attached to a thiol group of a molecule.

SUMMARY OF THE EMBODIMENTS

Fluorescent dyes or fluorophore compounds are suitable for use in various chemical and biological processes. Various embodiments are directed to fluorophores having a reactive group that can be used to couple or conjugate the fluorophore with another molecule such as a protein. Biosensors comprising fluorophores having a reactive group coupled or conjugated with a protein.

Additional embodiments are fluorophores having a reactive group and that have an emission wavelength of not less than about 575 nm, referred to as near-infrared dyes (NIR dyes). In one embodiment, the fluorophores have an emission at about 650 nm. The fluorophore embodiments include a pendant reactive group capable of conjugating with a member of a specific binding pair.

The fluorophores are suitable for coupling to receptors and to binding proteins having an affinity for a specific ligand or analyte. In various embodiments of the invention, the receptor or binding protein undergoes conformational changes when coupled to the ligand or analyte. The fluorophores when coupled to the binding protein exhibit a detectable signal change as a result of binding of ligand.

Another embodiment provides a fluorophore having a reactive moiety that can be covalently attached to an amino acid. The fluorophores in one embodiment have a thiol-reactive group that can be conjugated to a cysteine residue of a protein amino acid. Examples of suitable thiol-reactive groups that can be introduced into the fluorophore include a halo-acetyl and particularly an iodoacetyl group. Other thiol-reactive groups include iodoacetamide, bromoacetamide, iodoacetate or maleimide.

A further embodiment of the invention provides a fluorophore having a thiol-reactive group and having an emission of at least about 575 nm. The fluorophores in one embodiment of the invention are benzodioxazole, squaraine, 9-diethylamino-5H-benzo phenoxazin-5-one (hereinafter referred to as Nile Red), coumarin, and aza coumarin. In another embodiment, the invention is directed to derivatives of squaraine, benzodioxazole, Nile Red, coumarin and aza coumarin, hereinafter referred to interchangeably as squaraine nucleus or nuclei, benzodioxazole nucleus or nuclei, Nile Red nucleus or nuclei, coumarin nucleus or nuclei and aza coumarin nucleus or nuclei, respectively, or collectively as "fluorescent dye." Derivatives of the squaraine nuclei, benzodioxazole nuclei, Nile Red nuclei, coumarin nuclei and aza coumarin nuclei include any reaction product of the derivative, for example, with a protein amino acid group. Derivative is meant to include any chemical modification, addition, deletion, or substitution to an aforementioned nucleus. One embodiment includes nuclei of the aforementioned dyes that exhibit a fluorescence emission of at least about 575 nm are included as embodiments. In one embodiment, the squaraine nuclei, benzodioxazole nuclei, Nile Red nuclei, coumarin nuclei and aza coumarin nuclei contain a thiol-reactive group for binding to a protein.

Another embodiment is also directed to a conjugate of a binding protein and a squaraine nucleus, benzodioxazole nucleus, Nile Red nucleus, coumarin nucleus and aza coumarin nucleus coupled to the binding protein through a cysteine residue on the binding protein. The cysteine residue of the protein can be naturally occurring or engineered into the protein. In one embodiment, the binding protein is a glucose binding protein that has an affinity for glucose and reversibly binds glucose. The fluorophore produces a detectable change in a fluorescence property in response to binding. The detectable change in a fluorescent property can be a shift in the wavelength of emission, a change in intensity of the emitted energy, a change in fluorescence lifetime, a change in anisotropy, change in polarization, or a combination thereof. In another embodiment, the binding protein is a maltose binding protein (MBP) that has an affinity for and binds maltose. In another embodiment, the binding protein is altered so that it has an affinity for and binds non-native ligands.

The various embodiments of the present invention provide for a fluorophore having the formula

where A is selected from the group consisting of squaraine nucleus, Nile Red nucleus, benzodioxazole nucleus, coumarin nucleus, and an aza coumarin nucleus, and where Y is

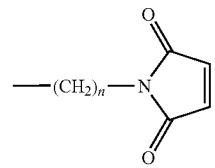

where n is an integer of 1 to 6, or Y is A'-CO—$R^1$, where A' is —$R^2$O— or —$R^2N(R^3)$—, where $R^2$ is a $C_1$ to $C_6$ alkyl, $R^3$ is H or $CH_3$, and $R^1$ is $CH_2Cl$, $CH_2Br$, $CH_2I$, or

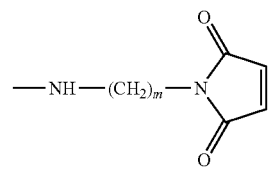

where m is an integer of 2 to 6.

Additional embodiments provide for a biosensor compound having the formula

where A is a fluorophore selected from the group consisting of a squaraine nucleus, a Nile Red nucleus, a benzodioxazole nucleus, a coumarin nucleus, and an aza coumarin nucleus, where Y'—B is

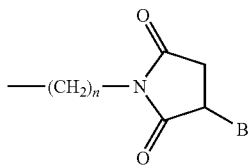

where n is an integer of 1 to 6, or Y'—B is A'-CO—V—B, where A' is —$R^2O$— or —$R^2N(R^3)$— where $R^2$ is a $C_1$ to $C_6$ alkyl, $R^3$ is H or $CH_3$, and V—B is —$CH_2$—B or

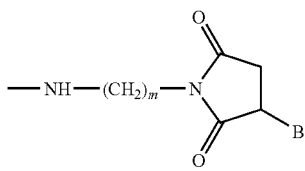

where m is an integer of 2 to 6, and B is a receptor having a reversible binding affinity for a ligand to be detected, and where the biosensor compound exhibits a detectable change in a fluorescence property as a result of changes in concentration of the ligand.

Further embodiments are methods for detecting analyte comprising: providing a biosensor compound having at least one mutated binding protein with a fluorophore covalently bonded thereto through a thiol group of said binding protein, where the fluorophore exhibits an emission fluorescence of at least 575 nm and is selected from the group consisting of a squaraine nucleus, Nile Red nucleus, benzodioxazole nucleus, and aza coumarin nucleus. The biosensor compound is subjected to an energy source to excite said fluorophore and to detect a fluorescence property as an indicator of a analyte concentration in the analyte-containing source.

BRIEF DESCRIPTION OF THE DRAWINGS

The following is a brief description of the drawings, in which.

DETAILED DESCRIPTION OF EMBODIMENTS OF THE INVENTION

Figure 1:
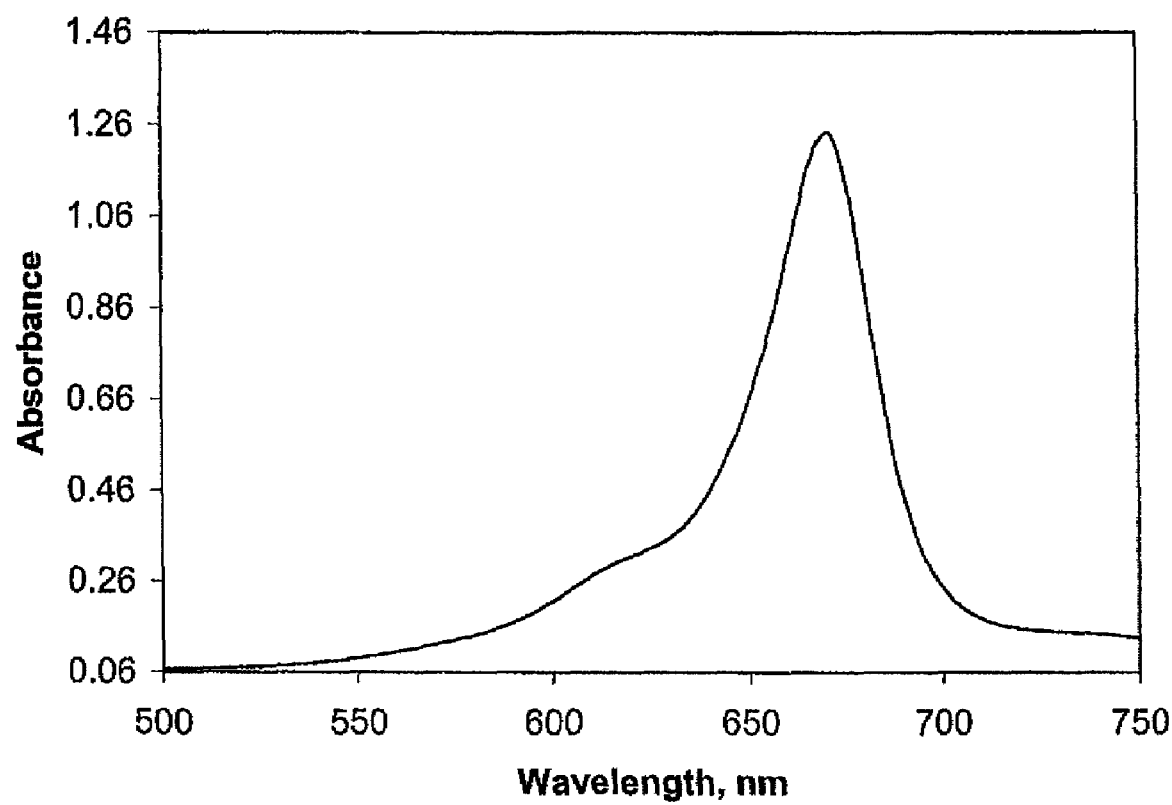
FIG. 1 is a graph showing the absorbance spectrum of compound 2 in chloroform.

The present disclosure is directed to fluorescent dyes that are suitable for use as components of biosensors for detecting a ligand and particularly an analyte, and methods of use. One embodiment is directed to fluorescent dyes that can be conjugated to a receptor to detect, quantify, or detect and quantify the ligand.

In one embodiment, the fluorescent dyes are used to produce a biosensor where the fluorescent dye is covalently attached to a binding protein. As used herein, the term "biosensor" and "biosensor compound" refers to a compound that undergoes a detectable change in specific response to a ligand or target analyte. The embodiments of the biosensor discussed herein include a binding protein that is capable of binding to an analyte. In other embodiments, the biosensor of the invention is able to detect an analyte and to detect changes in the analyte concentration. In various embodiments, the protein may be chosen from the group of periplasmic binding proteins that includes, but is not limited to, glucose/galactose binding protein, maltose binding protein, allose-binding protein, arabinose-binding protein, dipeptide-binding protein, glutamic acid/aspartic acid-binding protein, glutamine-binding protein, Fe(III)-binding protein, histidine-binding protein, leucine-binding protein, leucine/isoleucine/valine-binding protein, lysine/arginine/ornithine-binding protein, molybdate-binding protein, oligopeptide-binding protein, phosphate-binding protein, ribose-binding protein, sulfate-binding protein, Zn(II)-binding protein, and vitamin B-12-binding protein.

In other embodiments, the biosensor is a fluorescent dye covalently attached to a binding protein, wherein the protein-dye conjugate exhibits a fluorescence emission of 575 nm or higher. In one embodiment, the fluorescent dye exhibits a fluorescence emission of not less than 575 nm. In one exemplary form, the binding protein is a glucose/galactose binding protein (GGBP) that is able to bind with glucose when in contact with a glucose-containing source. In another embodiment, the binding protein is a maltose binding protein (MBP). Not to be held by any theory, the binding protein is understood to undergo a conformational change upon binding of ligand. The percentage of binding protein binding sites occupied by ligand is dependent upon the concentration of ligand and the binding constant of the binding protein.

The fluorescent dye embodiments that exhibit a fluorescence emission of at least about 575 nm avoid or minimize background interference from the biological system or other components in the glucose source. The fluorescent dyes exhibit a change in intensity of the fluorescence signal, a shift in the emission wavelength of the maximum fluorescence emission, a change in fluorescence lifetime, a change in anisotropy, a change in polarization, or a combination thereof, when the binding protein undergoes a conformational change as a result of changes in the glucose concentration. In the method embodiment, the biosensor contacts a sample containing analyte, for example glucose, to enable the analyte to bind with the binding protein, where the sample includes, but is not limited to, blood, saliva, interstitial fluid, etc. An energy source, such as a laser or LED, is applied to the biosensor to excite the fluorescent dye, and a fluorescence property is detected. Due to either a conformational change in the binding protein, subsequent changes in the microenvironment of the dye, or both, the detected fluorescence property or change of the detected fluorescence property can be correlated to the presence of an analyte or a analyte concentration. The fluorescence and detection can be carried out continuously or intermittently at predetermined times. Thus, episodic or continuous sensing of analyte, for example, glucose, is envisaged. The biosensor disclosed herein is adaptable for use in strips, implants, micro- and nano-particles, and the like.

The fluorescent dye is covalently attached to the binding protein in a site-specific manner to obtain the desired change in the fluorescence. The fluorescent dye is attached at a site on the binding protein so that the conformational change maximizes the change in fluorescence properties. In other embodiments of the invention, the fluorescent dyes have a thiol-reactive group that can be coupled to the thiol group on a cysteine residue of the binding protein. The fluorescent dye includes the aforementioned derivatives of the squaraine nuclei, benzodioxazole nuclei, Nile Red nuclei, coumarin nuclei and aza coumarin nuclei.

The biosensor in one embodiment has the formula I

   (I)

In the formula I, A is squaraine nucleus, Nile Red nucleus, benzodioxazole nucleus, coumarin nucleus, aza coumarin nucleus, and derivatives thereof, Y'—B is

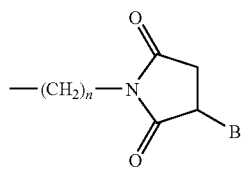

where n is an integer of 1 to 6, or Y'—B is A'-CO—V—B, where A' is —$R^2O$— or —$R^2N(R^3)$—. $R^2$ is a $C_1$ to $C_6$ alkyl. In one embodiment, $R^2$ is a $C_2$ to $C_4$ alkyl. $R^3$ is H or $CH_3$. V—B is —$CH_2$—B or

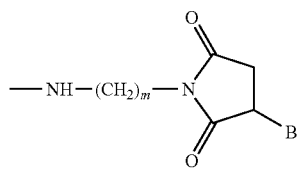

where m is an integer of 2 to 6. In one embodiment, $R^2O$ is —$CH_2CH_2O$—. In another embodiment, $R^2N(R^3)$ is —$CH_2CH_2NH$—. B is a receptor having a binding affinity for a ligand being detected and monitored by the biosensor. The biosensor compound exhibits a detectable change in a fluorescence property as a result of changes in concentration of the ligand. In one embodiment, B is a glucose/galactose binding protein that exhibits a detectable change in fluorescence emission as a result of changes in concentration of the ligand such as glucose. In another embodiment, B is a maltose binding protein.

In one embodiment, fluorescent dyes or fluorophores have a thiol-reactive group and have the general formula

   (II)

where A is a squaraine nucleus, Nile Red nucleus, benzodioxazole nucleus nucleus, coumarin nucleus, aza coumarin nucleus, or derivative thereof and Y is a thiol-reactive group.

In other embodiments, in formula II, Y is

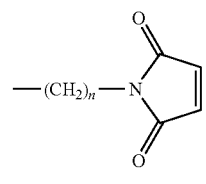

where n is an integer of 1 to 6, or Y is A'-CO—$R^1$. A' is —$R^2O$— or —$R^2N(R3)$—. $R^2$ is a $C_1$ to $C_6$ alkyl. In one embodiment, $R^2$ is a $C_2$ to $C_4$ alkyl. $R^3$ is H or $CH_3$. $R^1$ is $CH_2Cl$, $CH_2Br$, —$CH_2I$, or

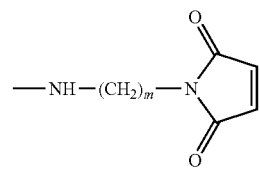

where m is an integer of 2 to 6. The dye may exhibit a fluorescence emission of at least about 575 nm. In one embodiment, $R^2O$ is —$CH_2CH_2O$—. In another embodiment, $R^2N(R^3)$ is —$CH_2CH_2NH$—. In a further embodiment, Y is —$(CH_2)_2OCOCH_2CH_2X$, where X is Cl, Br or I. In other embodiments, $R^2$ is a $C_2$ to $C_4$ alkyl such as —$CH_2CH_2$—.

The squaraine nucleus as embodiments of the invention are based on derivatives of the squaraine structure

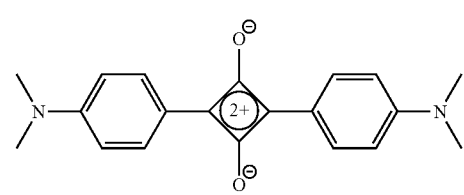   (III)

The squaraine nucleus of formula III exhibits changes in its fluorescence properties with changes in its environment. For example, the squaraine nucleus III exhibits a 20-fold increase in its fluorescence quantum yield by changing its environment from a polar protic solvent such as methanol to a non-polar solvent such as toluene [C. Cornelissen-Gude, W. Rettig, R. Lapouyade. "Photophysical properties of Squaraine Derivatives: Evidence for Charge Separation." *J. Phys. Chem. A* 1997, 101, 9673-9677]. Squaraine dyes can have an absorbance maximum near 635 nm and exhibit a fluorescence emission peak at about 650 nm. These dyes can fluoresce readily when exposed to the light from a red laser diode excitation source, for example.

The thiol-reactive squaraine nucleus embodiments of the invention have the structures of formula IV and formula V

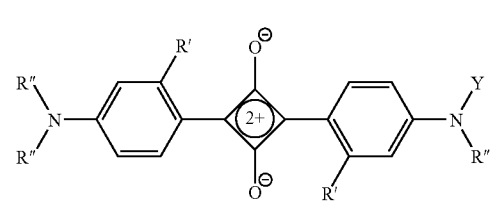   (IV)

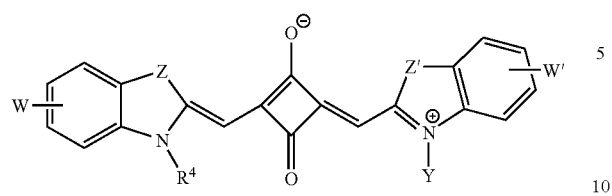
(V)

where R' is H or OH, R" are independently methyl, ethyl or propyl, $R^4$ is a $C_1$ to $C_6$ alkyl or $(CH_2)_q CO_2 H$, where q is an integer of 1 to 5, Z and Z' are independently S, O, or $C(CH_3)_2$, W and W' are independently H, $CH_3$, $SO_3H$, fused benzene, or fused sulfobenzene, and Y is as previously defined.

In one embodiment, the thiol-reactive squaraine nucleus has the formula

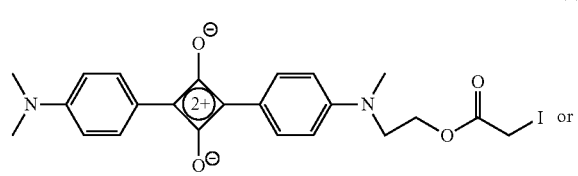
(1)

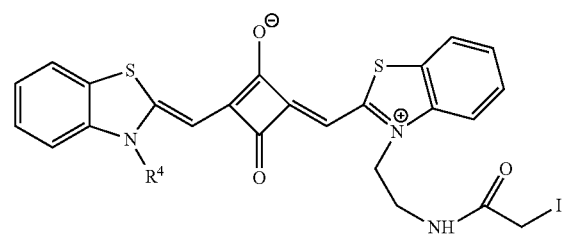
(2), (3)

where $R^4$ is ethyl in compound 2 or $(CH_2)_2 CO_2 H$ in compound 3.

Another embodiment includes Nile Red nuclei generally having an absorbance of about 550 nm and emission maxima of about 575 nm or more. These nuclei typically exhibit a shift of the emission maxima to as much as 650 nm in lipid environments. In one embodiment, Nile Red nuclei have the formula

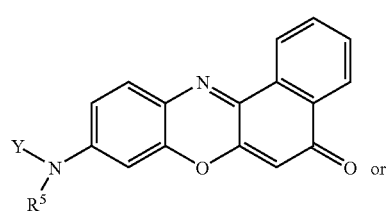
(VI)

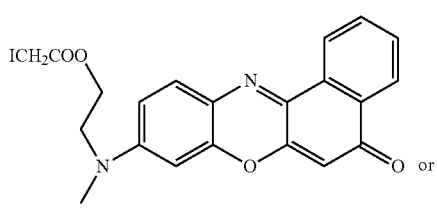
(VII)

where $R^5$, $R^6$, and $R^7$ are independently methyl, ethyl or propyl, and Y is as previously defined.

In one embodiment, the Nile Red nucleus has the formula

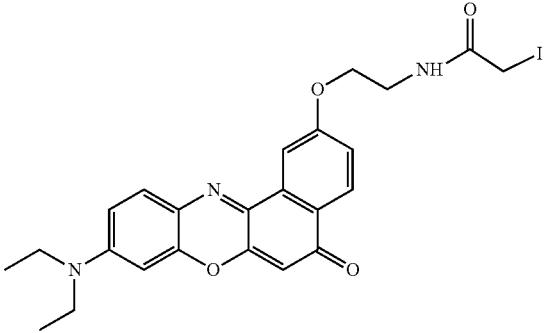
(4)

(5)

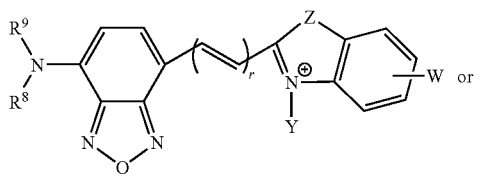

One embodiment includes benzodioxazole nuclei having the formula (VIII)

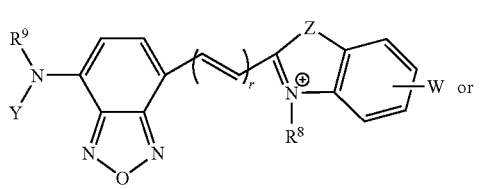

(VIIIa)

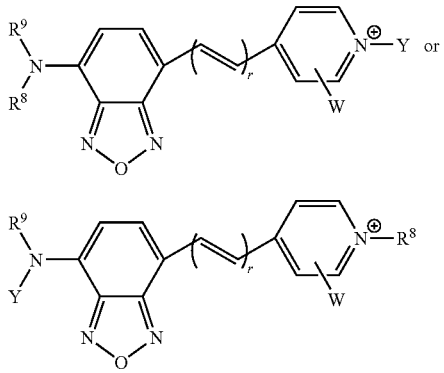
(IX)

(IXa)

where r is an integer of 1 to 3, $R^8$ and $R^9$ are independently a $C_1$ to $C_6$ alkyl or $(CH_2)_sCO_2H$, where s is an integer of 2 to 5. Z is S, O, or $C(CH_3)_2$. W is H, $CH_3$, $SO_3H$, fused benzene, or fused sulfobenzene. Y is as previously defined.

In one embodiment, the benzodioxazole nucleus has the formula

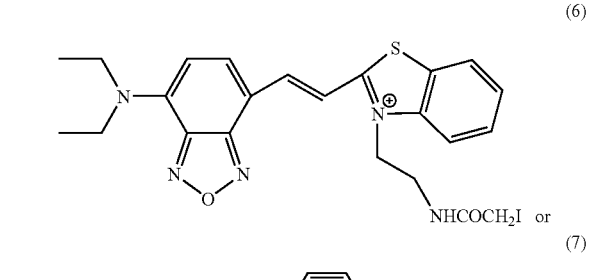
(6)

(7)

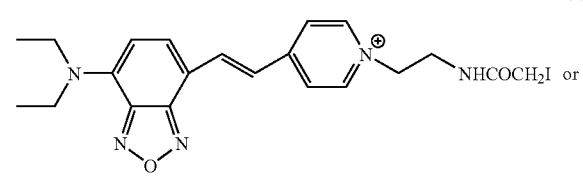
(8)

Another embodiment includes coumarin and aza coumarin nuclei having the formula

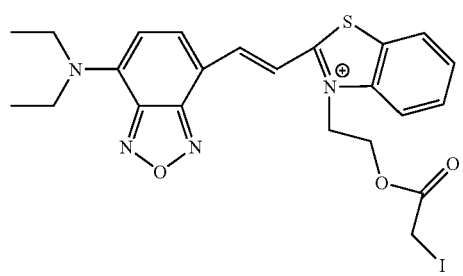
(X)

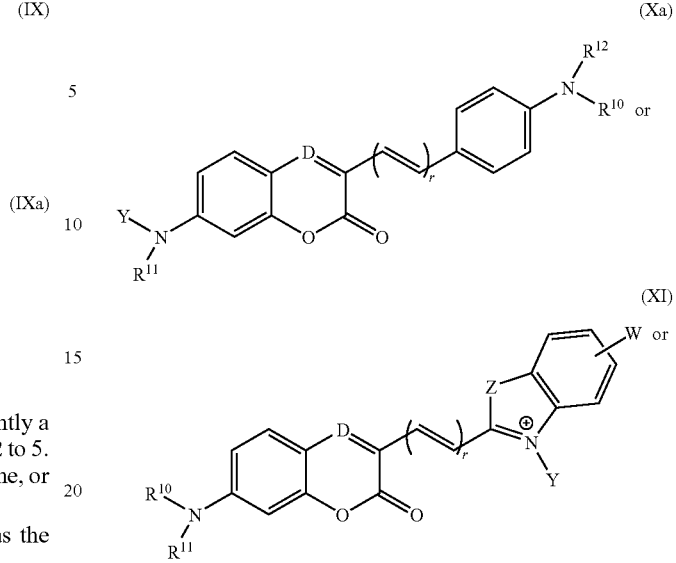
(Xa)

(XI)

(XIa)

where D is CH or N, r is an integer of 1 to 3, $R^{10}$, $R^{11}$ and $R^{12}$ are independently $C_1$ to $C_6$ alkyl or $(CH_2)_sCO_2H$, where s is an integer of 2 to 5, Z is S, O or $C(CH_3)_2$. W is H, $CH_3$, $SO_3H$, fused benzene or fused sulfobenzene and Y is as previously defined.

In one embodiment, the aza coumarin nucleus has the formula

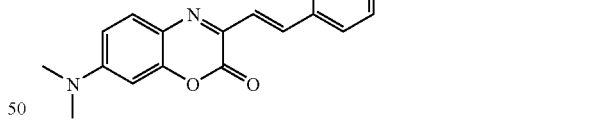
(9)

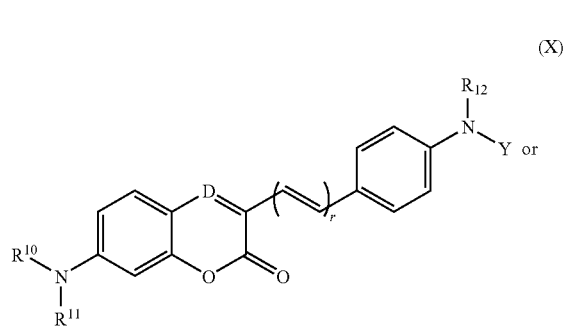
(10)

The squaraine nucleus embodiments of the invention can be synthesized by various known techniques. Symmetrical nuclei can be prepared by reacting an aromatic nucleophile with squaric acid. A first reaction scheme for producing an iodoacetyl squaraine is depicted in the Scheme I as follows.

Scheme I
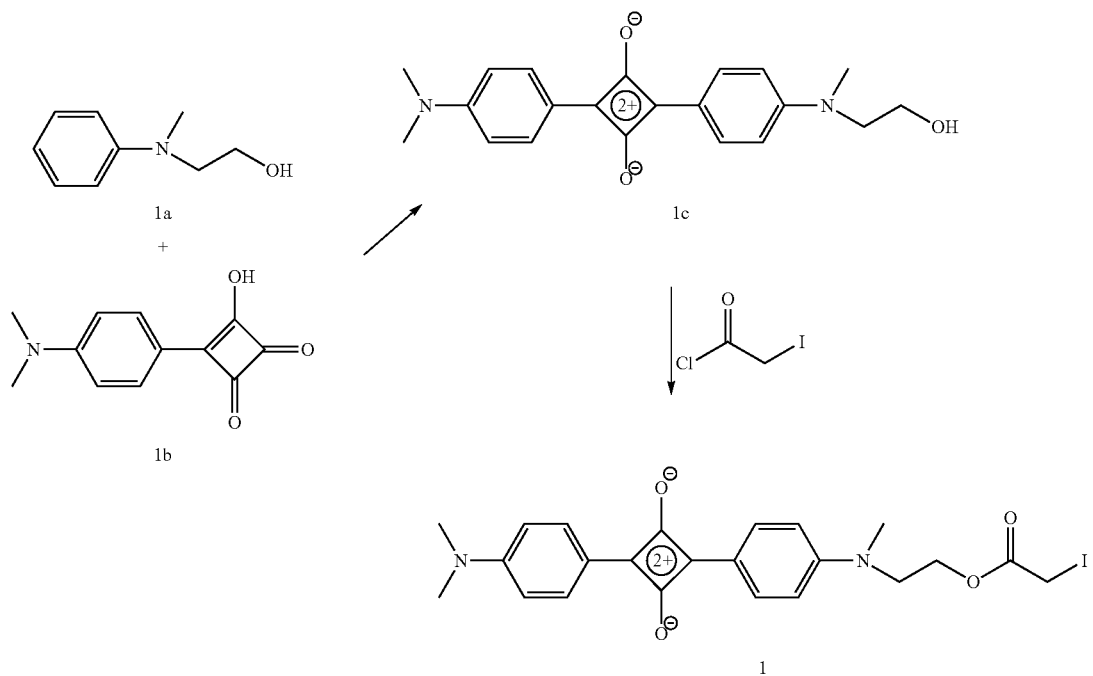
A second reaction scheme for producing an iodoacetamidyl squaraine nucleus derivative is depicted in the Scheme II as follows.
Scheme II
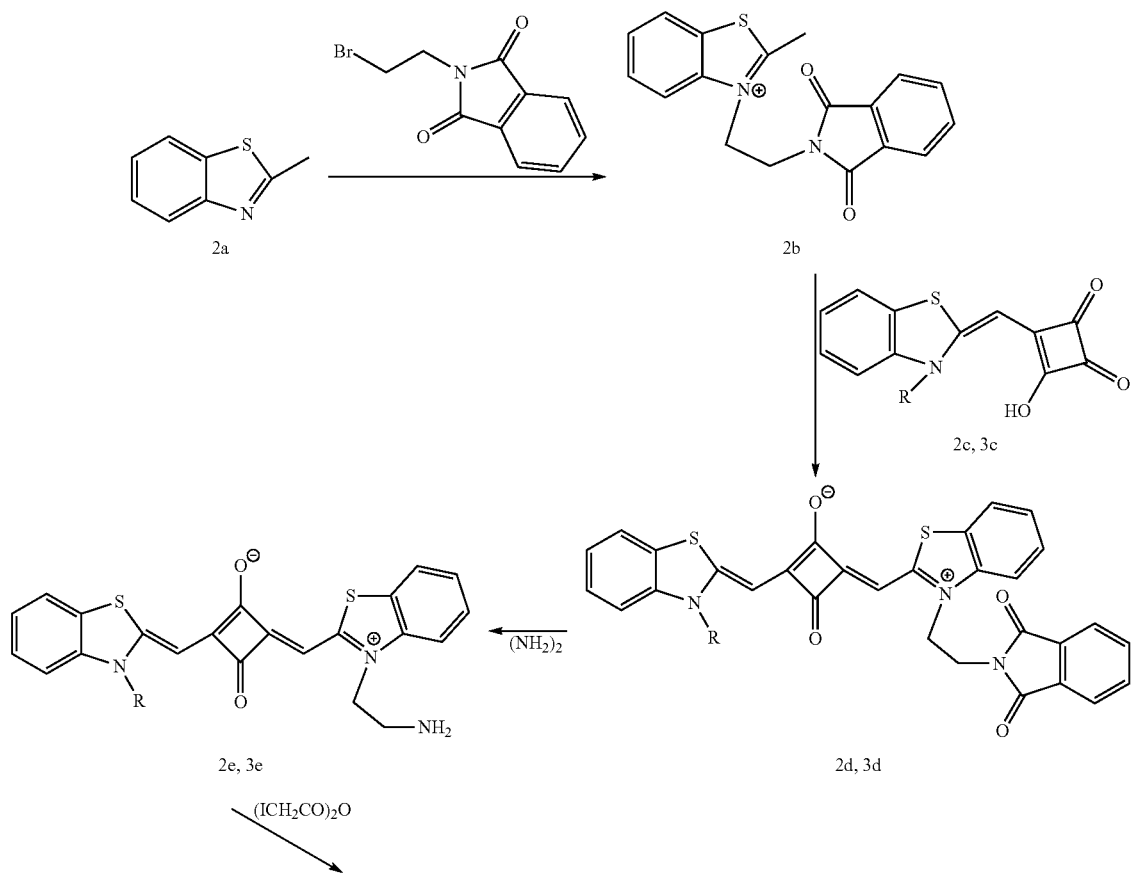

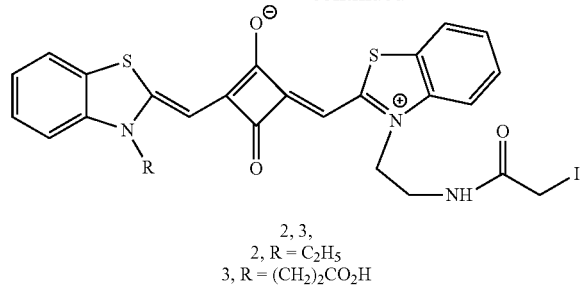
2, 3,
2, R = C₂H₅
3, R = (CH₂)₂CO₂H
The Nile Red nucleus derivative embodiments can also be prepared using various reaction schemes. A first reaction scheme for producing an iodoacetyl derivative is depicted in the Scheme III as follows.
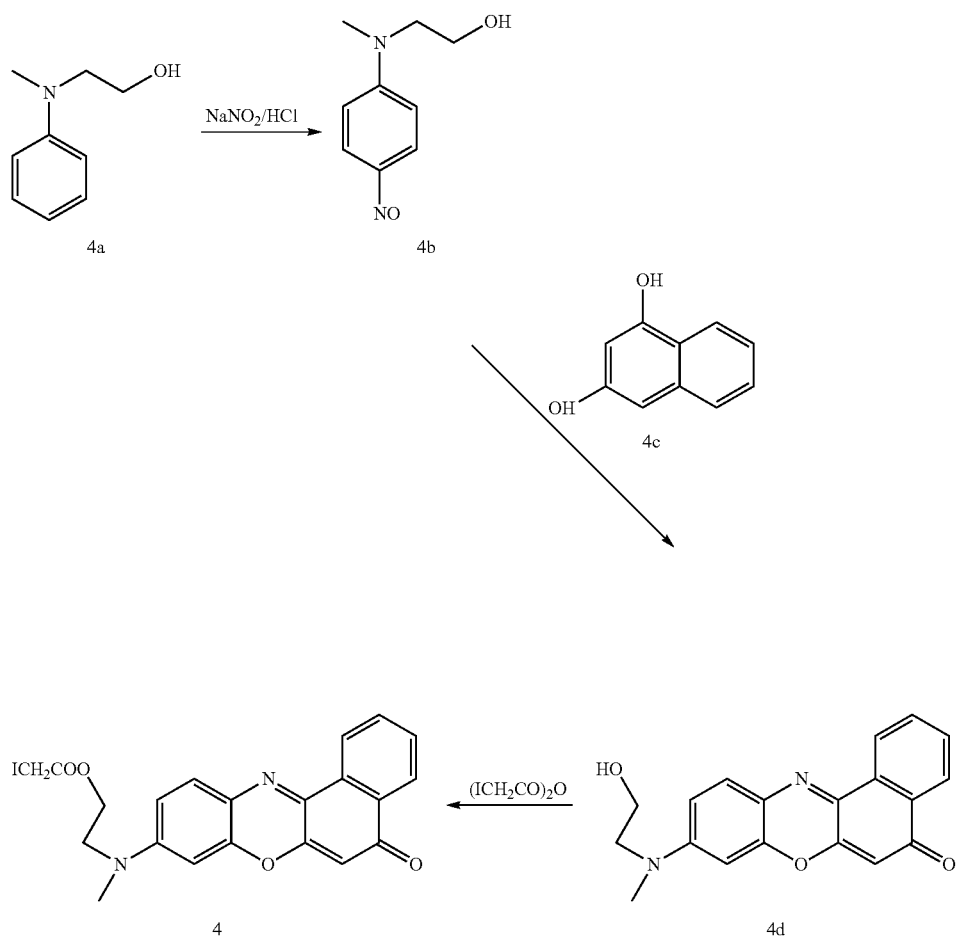

A second reaction scheme for producing an iodoacetamidyl derivative is depicted in the Scheme IV as follows.
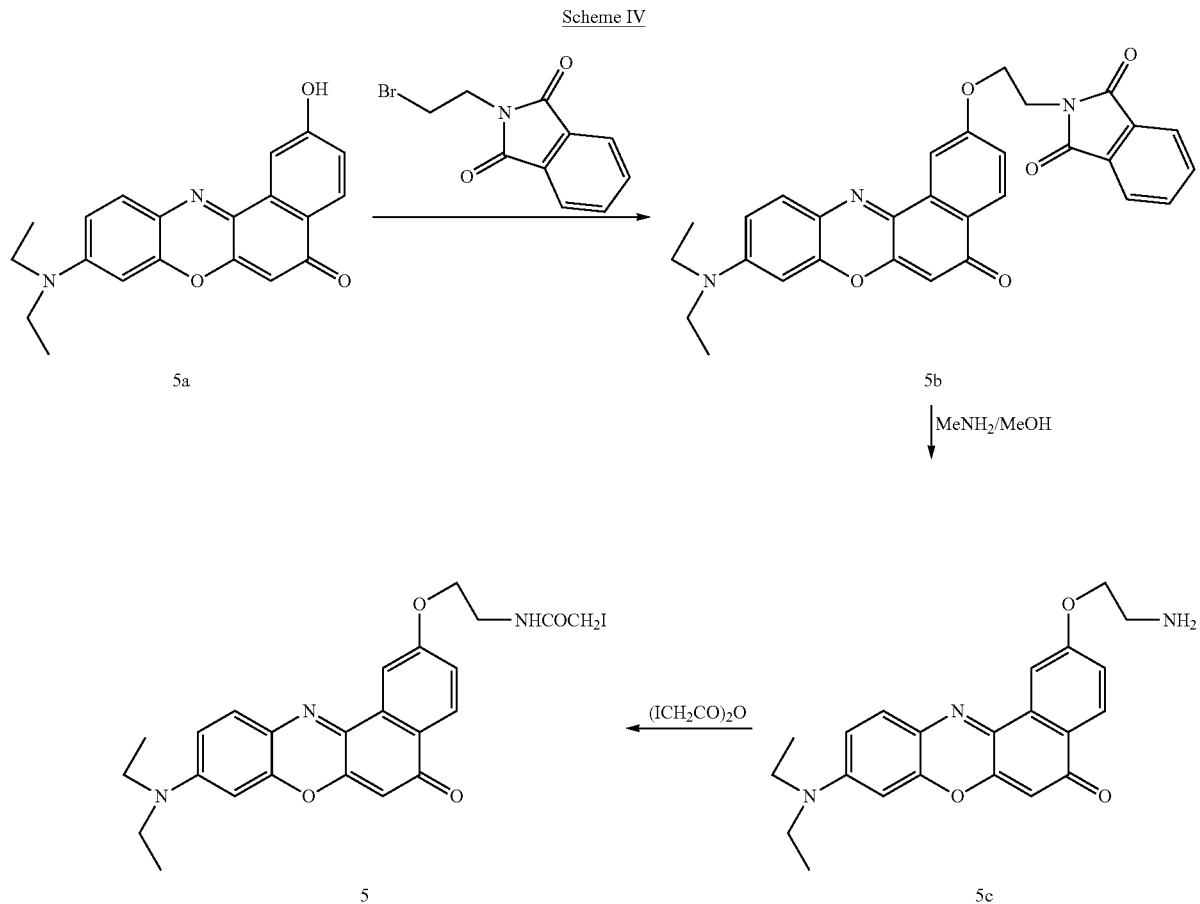
A procedure for producing the benzodioxazole nucleus derivative embodiments is depicted in the reaction Scheme V as follows.
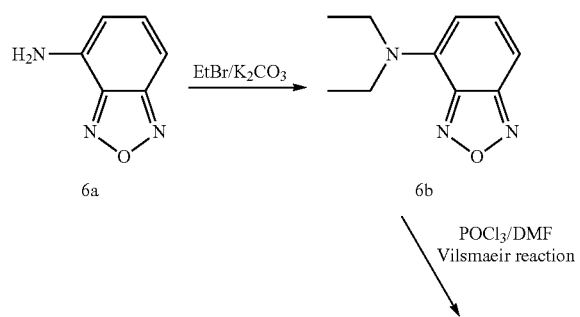

-continued
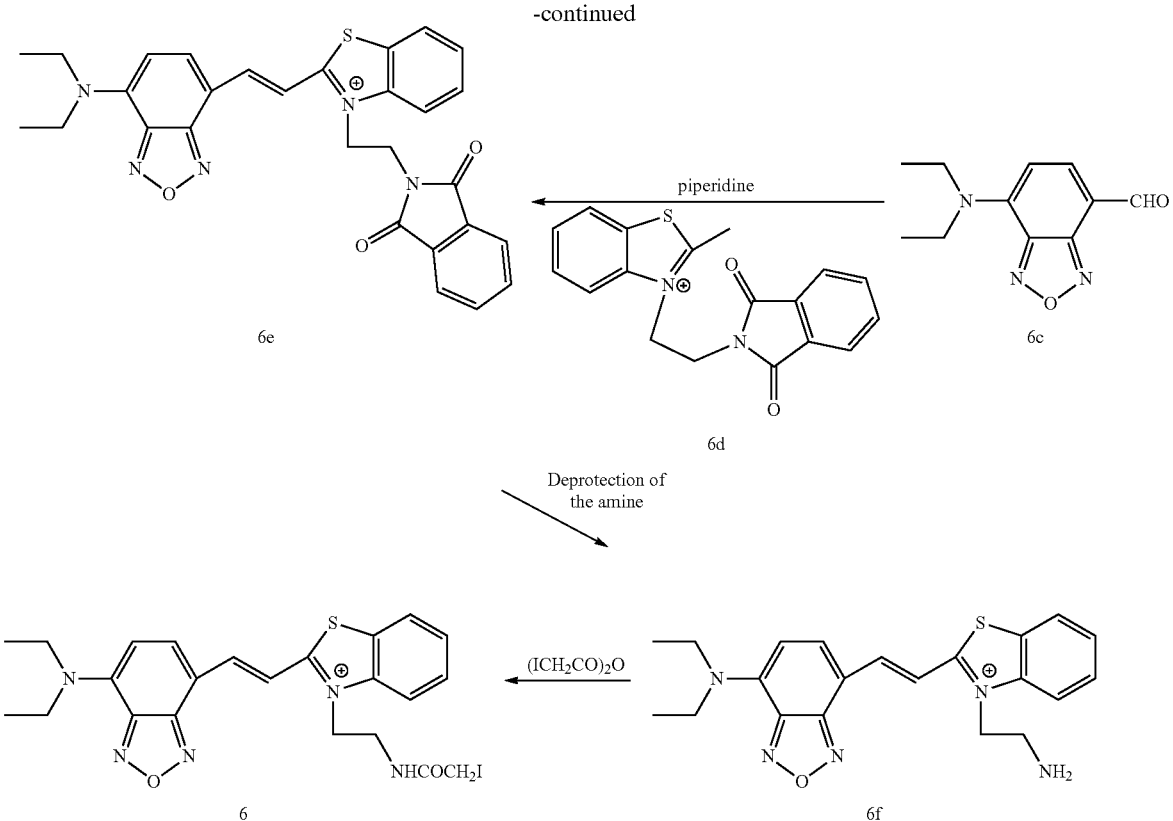
Scheme V can be modified to produce benzodioxazole nucleus derivatives containing other ring systems, as shown below in Scheme VI.
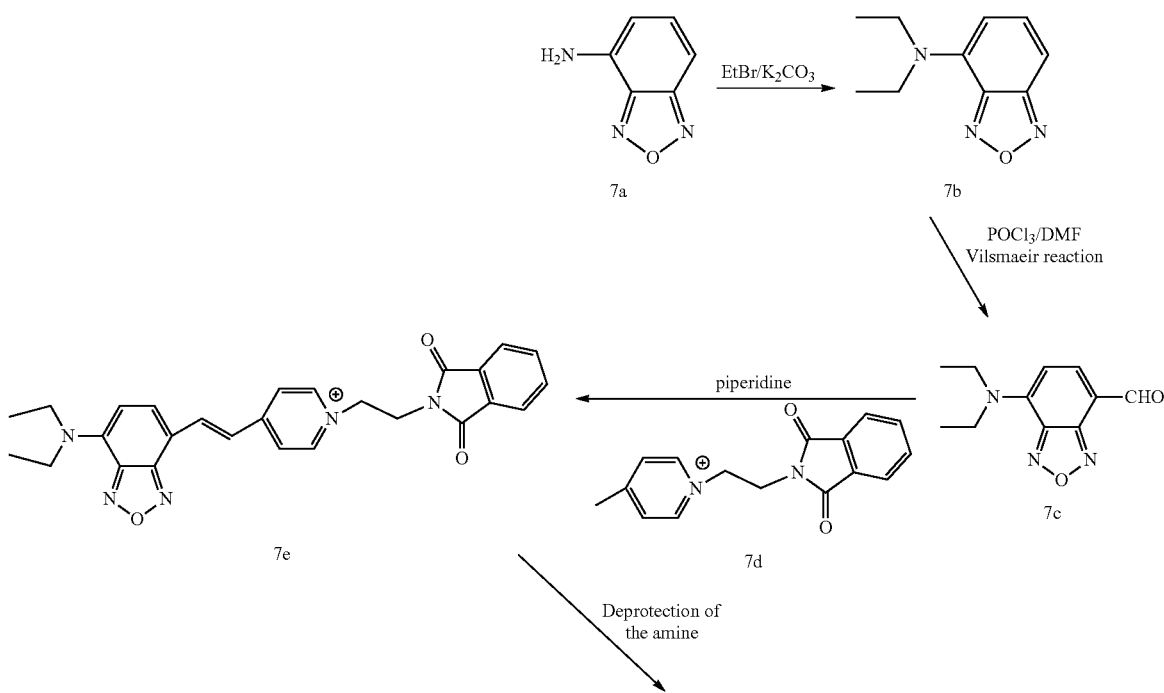

-continued
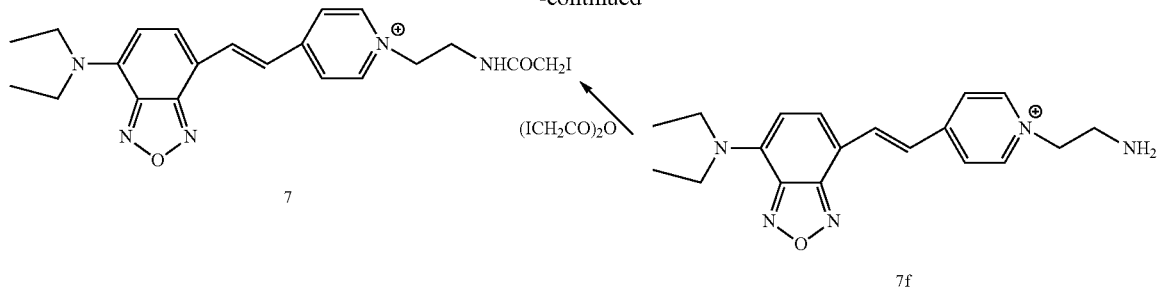
An alternative procedure for producing benzodioxazole nucleus derivatives is shown in reaction scheme VIa.
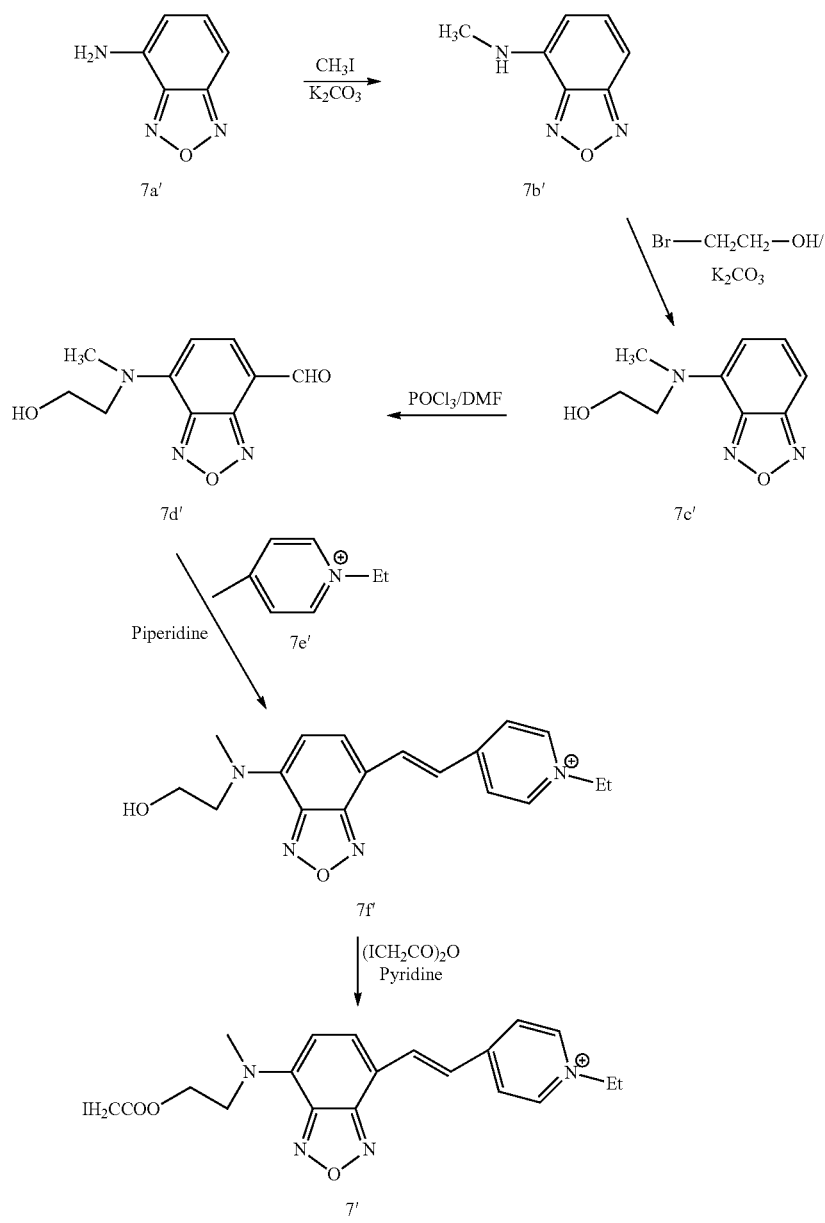

An exemplary procedure for the synthesis of benzodioxazole nucleus with an iodoacetyl linker is depicted in Scheme VII
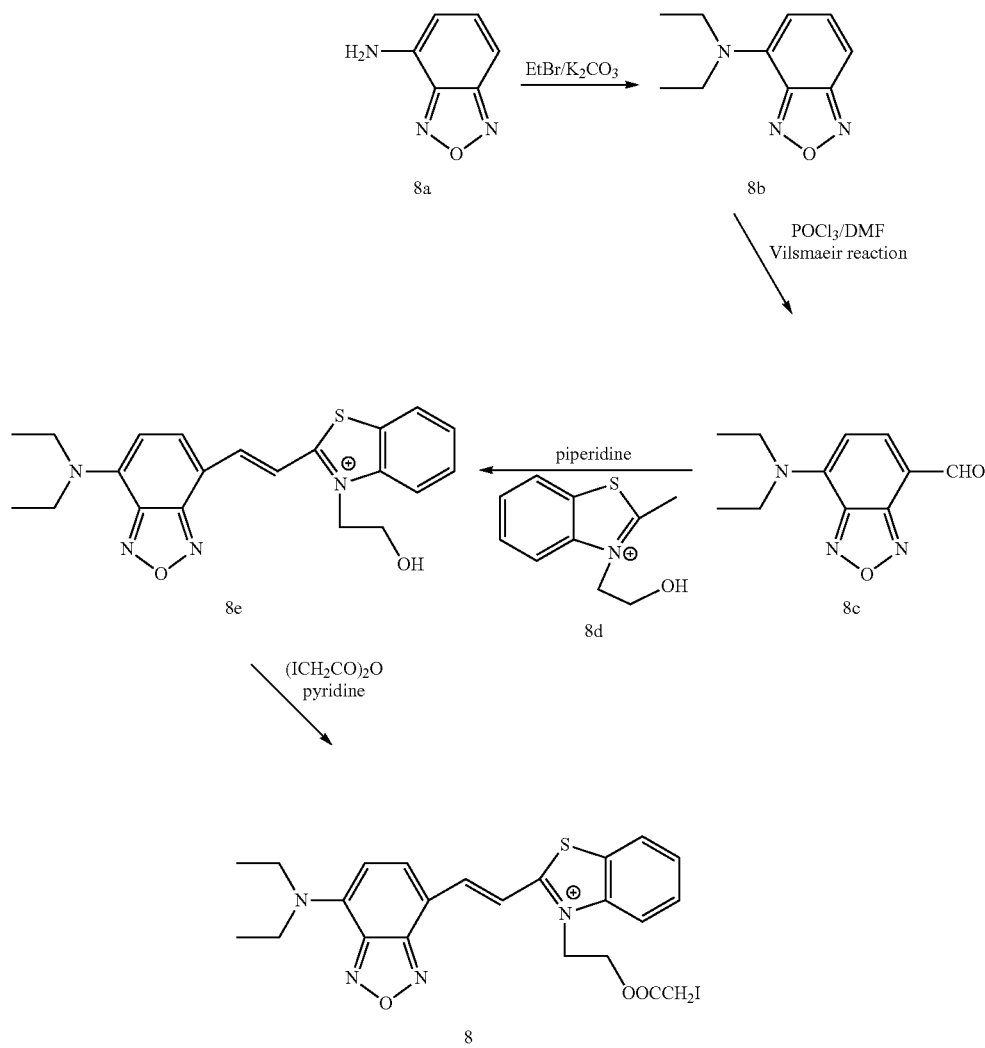
An alternative procedure for producing benzodioxazole nucleus derivatives is shown in the reaction Scheme VIIa.
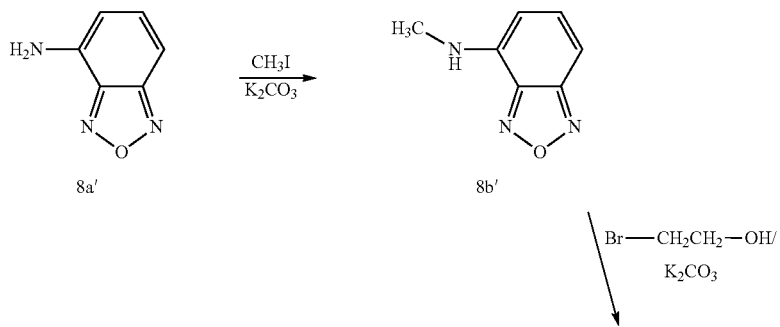

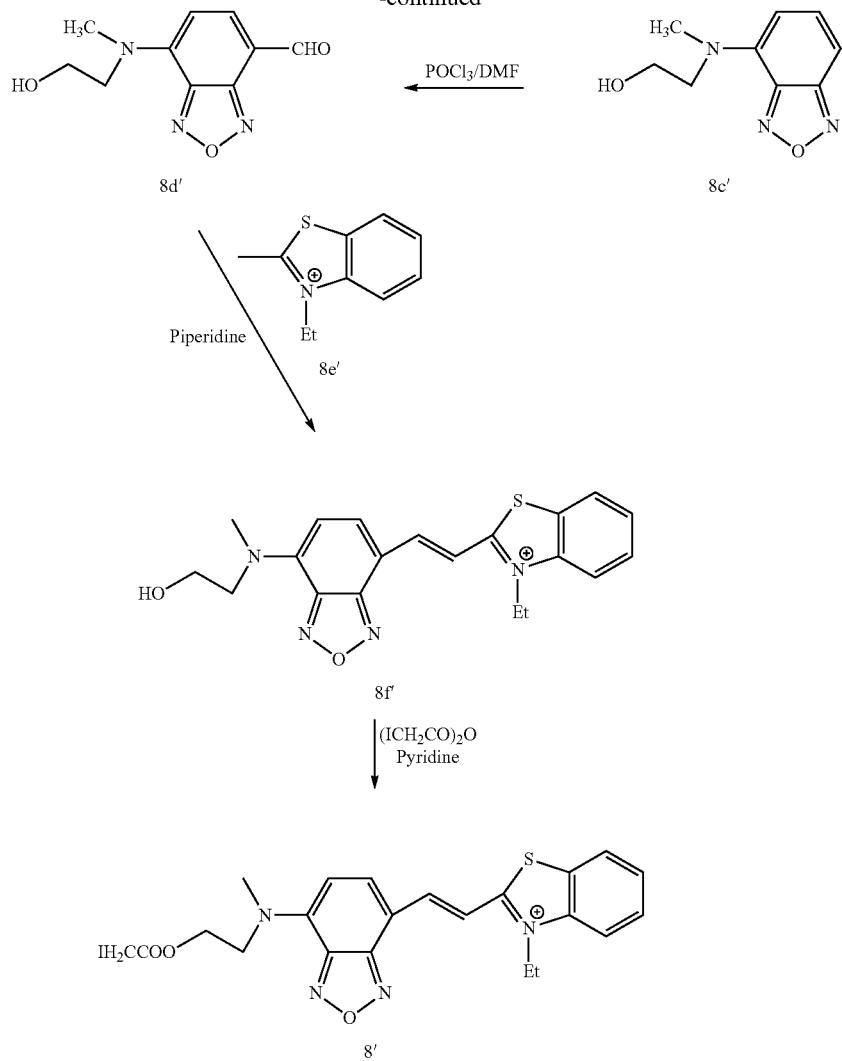
An exemplary procedure for producing the aza coumarin nucleus derivatives is depicted in the reaction Scheme VIII.
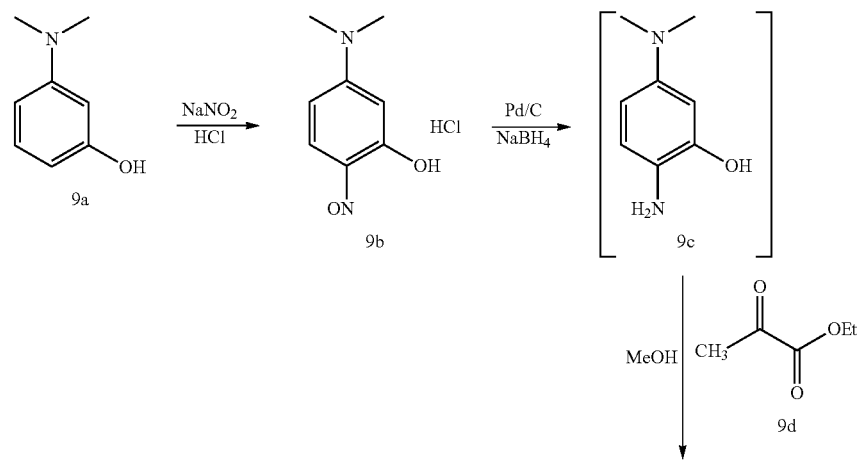

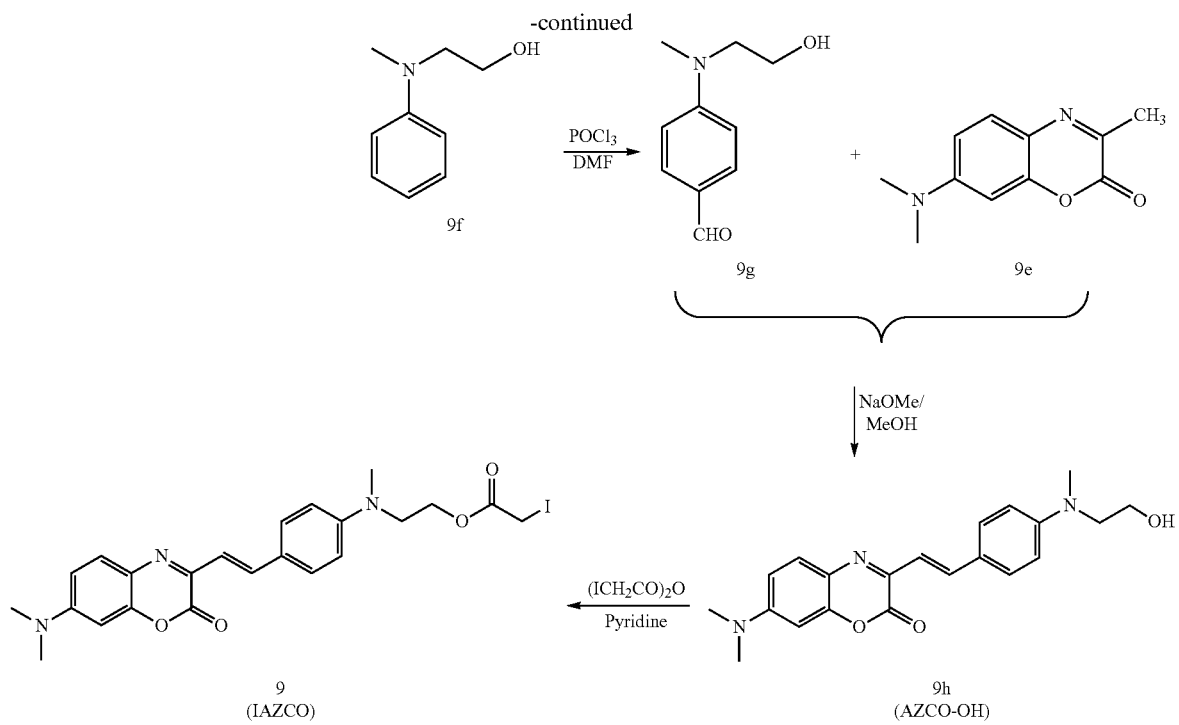
An alternative procedure for producing the aza coumarin nucleus derivatives is depicted in reaction Scheme VIIIa.
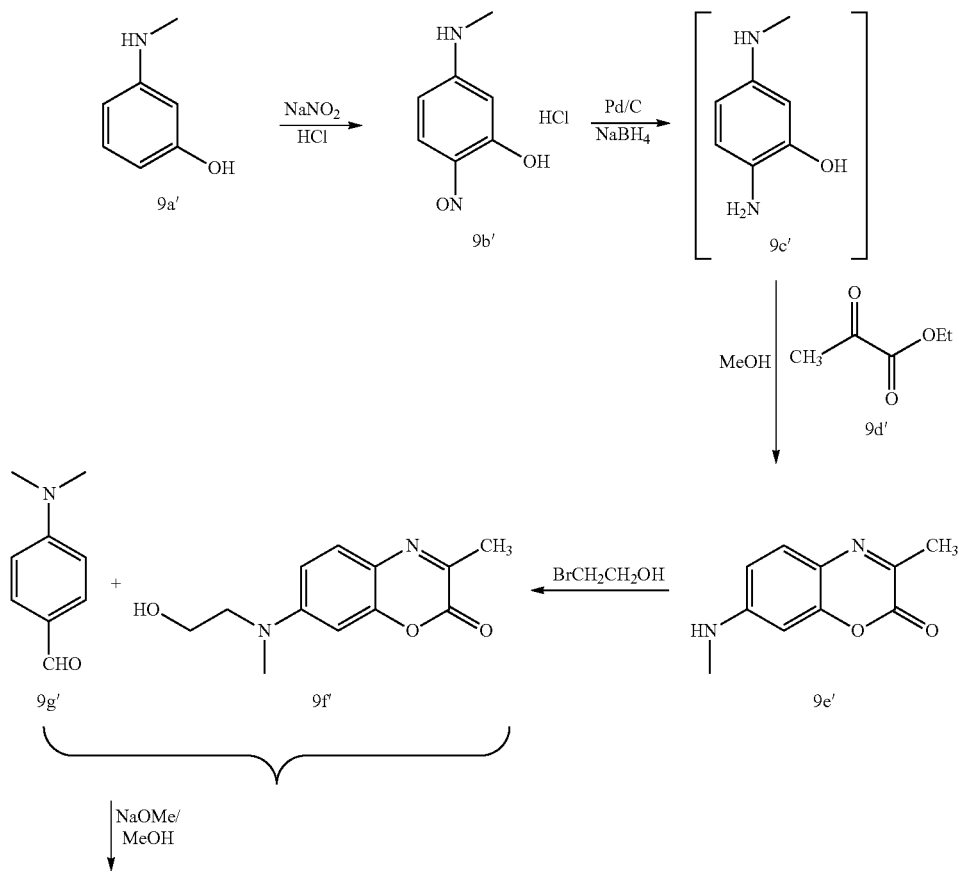

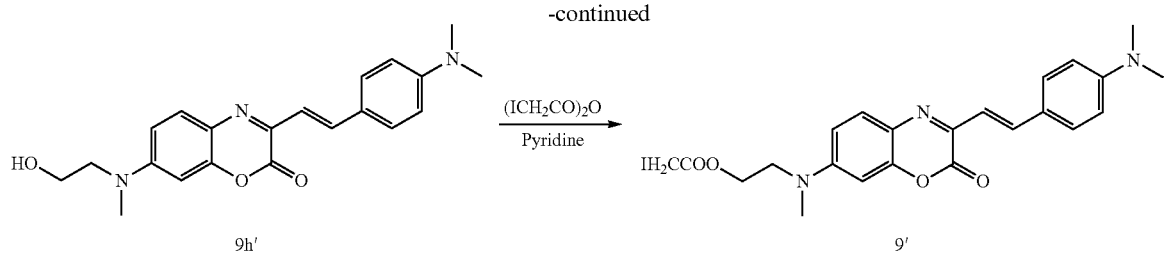
Another exemplary procedure for producing coumarin nuclei is depicted in reaction Scheme IX.
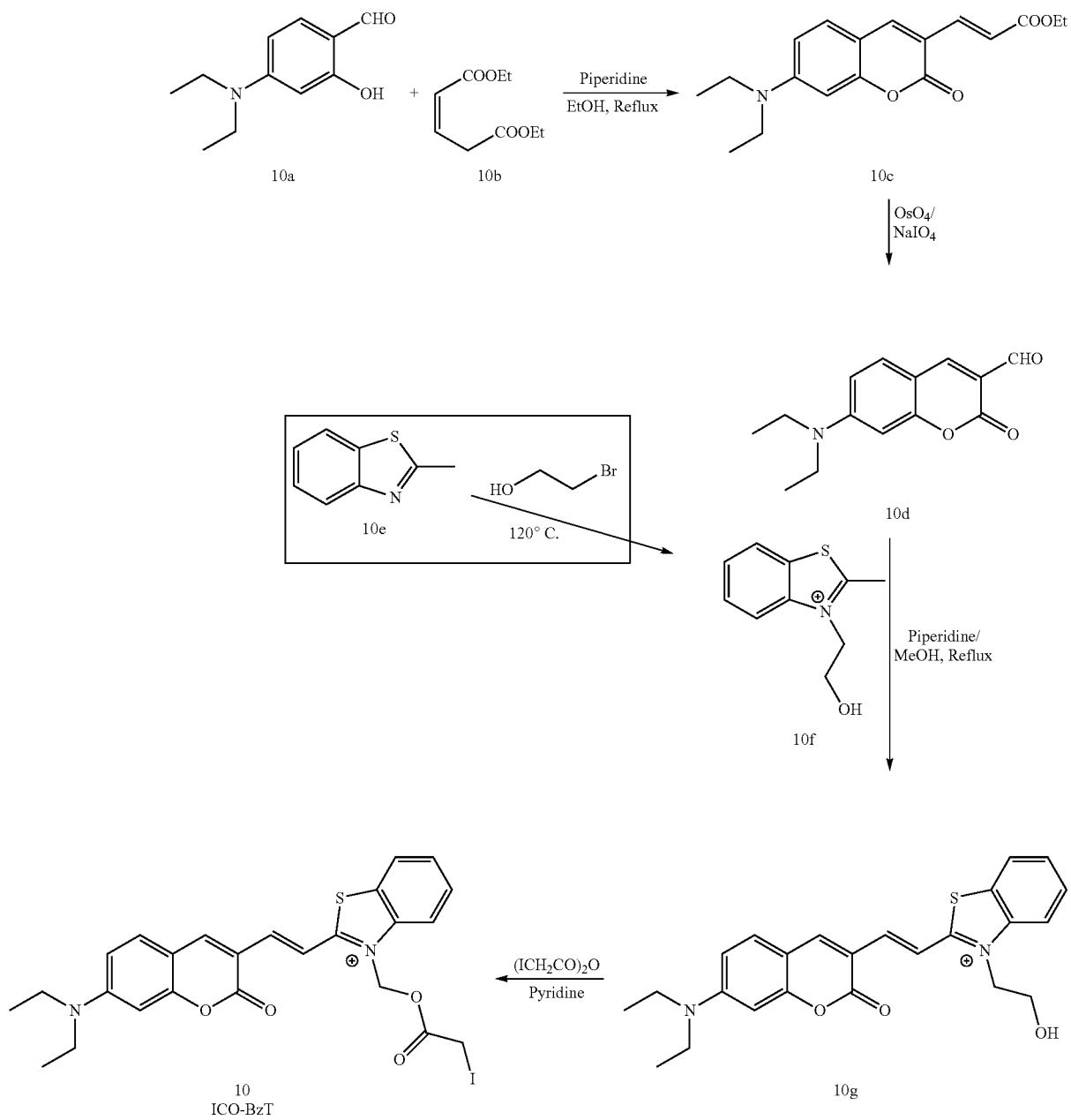

Another procedure for producing the coumarin nucleus derivatives is depicted in reaction Scheme IXa.

Scheme IXa

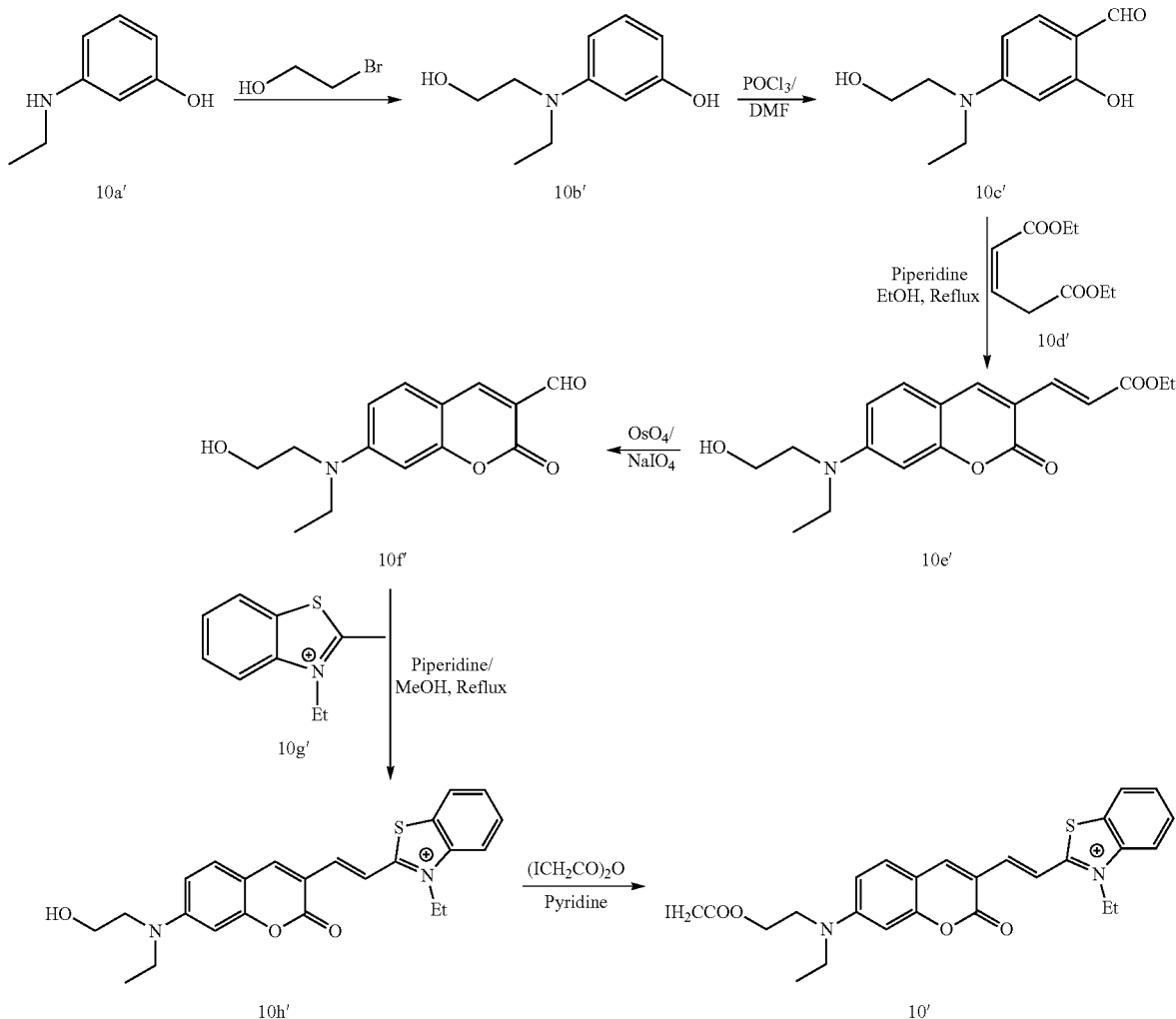

In another embodiment of the invention, benzodioxazole, squaraine, Nile Red, coumarin, and aza coumarin nuclei have a fluorescence emission. In one embodiment, the specific fluorescent nuclei described above have fluorescent emission above about 575 nm.

In one embodiment, the resulting thiol-reactive nuclei are reacted with a binding protein to produce fluorescent binding protein conjugates useful as biosensors.

In one embodiment the resulting squaraine nucleus-binding protein conjugates have the Markush formulas:

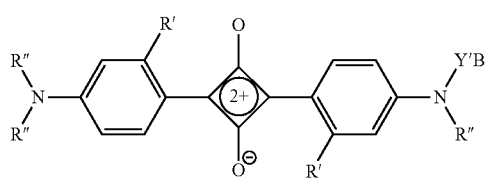

-continued

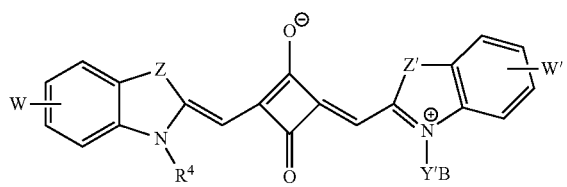

where Y'—B is

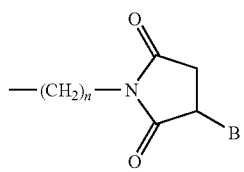

where n is an integer of 1 to 6, or Y'—B is A'-CO—V—B, where A' is —R²O— or —R²N(R³)—. R² is a $C_1$ to $C_6$ alkyl. In one embodiment, R² is a $C_2$ to $C_4$ alkyl. R³ is H or $CH_3$. V—B is —$CH_2$—B or

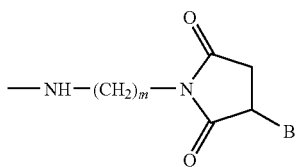

where m is an integer of 2 to 6. In one embodiment, R²O is —$CH_2CH_2O$—. In another embodiment, R²N(R³) is —$CH_2CH_2NH$—, and where B is binding protein.

In one embodiment the resulting Nile Red nucleus-binding protein conjugate has the Markush formulas:

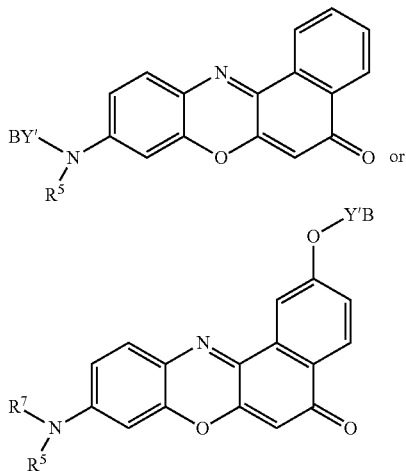

where Y'B is as previously defined and B is binding protein.

In one embodiment the resulting benzodioxazole nucleus-binding protein conjugate has the Markush formulas:

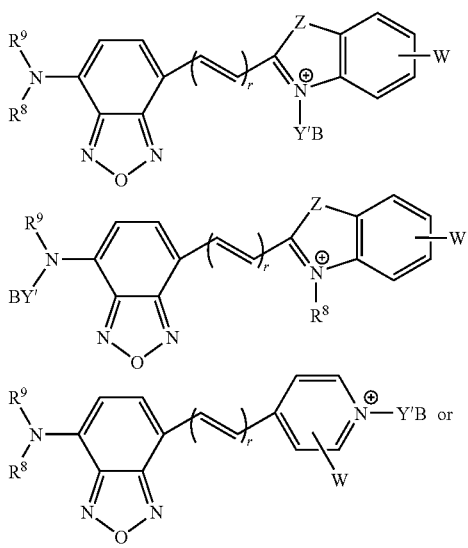

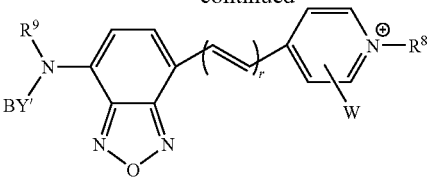

where Y'B is as previously defined and B is binding protein.

In one embodiment the resulting coumarin, and aza coumarin nucleus-binding protein conjugate has the Markush formulas:

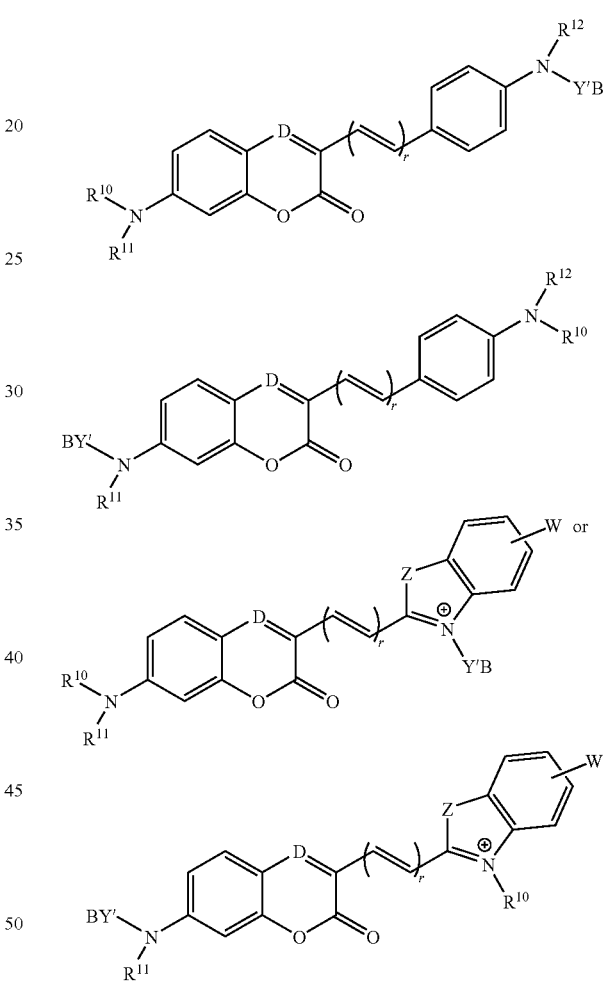

where Y'B is as previously defined and B is binding protein.

In one embodiment the resulting binding protein conjugate has the formula:

(XII)

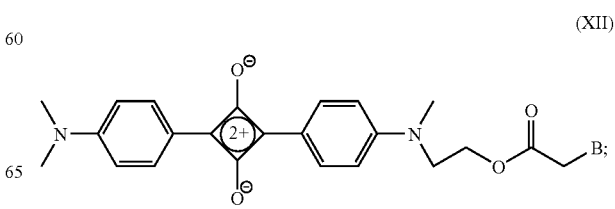

(XIII)

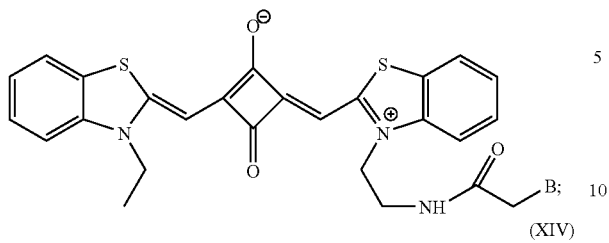

(XIV)

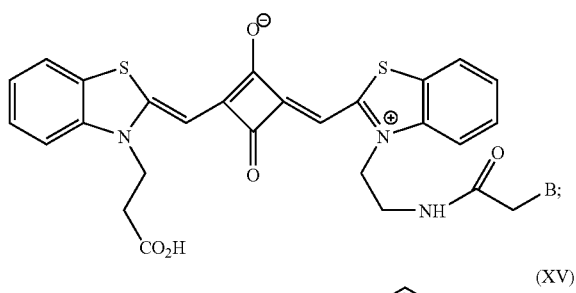

(XV)

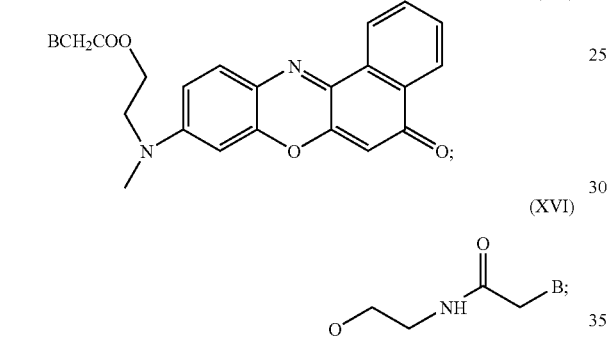

(XVI)

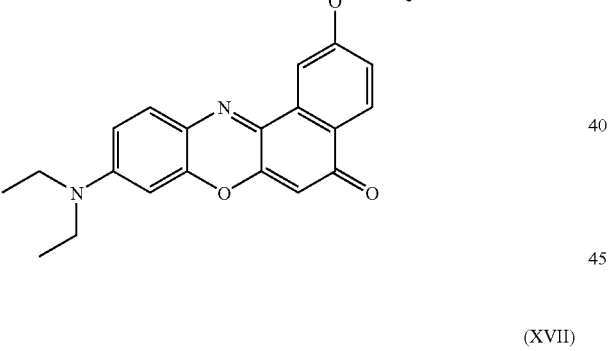

(XVII)

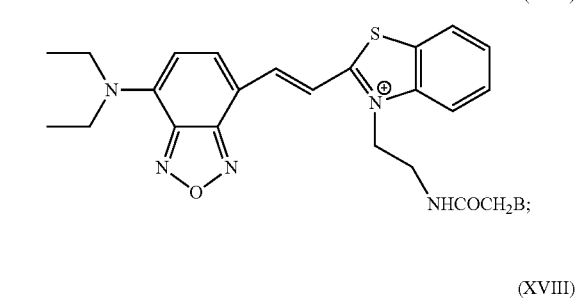

(XVIII)

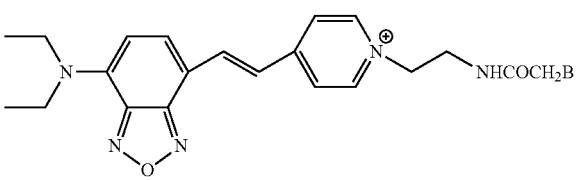

(XIX)

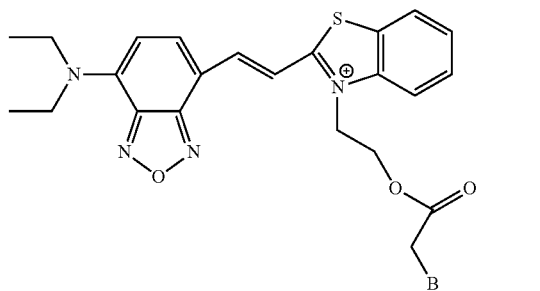

(XX)

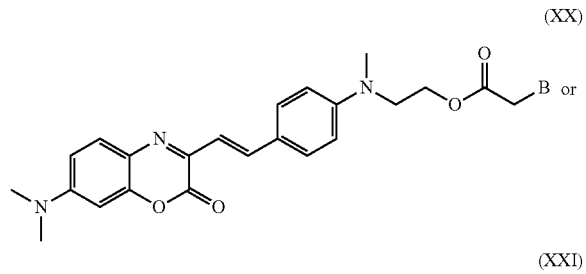

(XXI)

The binding proteins B include a thiol group, for example, a cysteine residue, that is able to react with the thiol-reactive fluorescent dye. The term "binding proteins" refers to proteins that interact with specific analytes in a manner capable of transducing or providing a detectable signal differentiable either from when analyte is not present, analyte is present in varying concentrations over time, or in a concentration-dependent manner, by means of the methods described. Capable of transducing or "provide a detectable signal", as used herein, refers to the ability to recognize a change in a property of a reporter group in a manner that enables the detection of ligand-protein binding. For example, in one embodiment, the mutated GGBPs comprise a detectable reporter group whose detectable characteristics alter upon glucose binding. The change in the detectable characteristics may be due to an alteration in the environment of the label attached to the mutated GGBP or a conformational change of the protein resulting from binding. The transducing or providing a detectable signal may be reversible or non-reversable. As used herein, the terms transducing and providing a detectable signal are used interchangeably. The transduction event includes continuous, programmed, and episodic means, including one-time or reusable applications. Reversible signal transduction may be instantaneous or may be time-dependent, providing a correlation with the presence or concentration of analyte is established. Binding proteins mutated in such a manner to effect transduction are embodiments of the present invention. Binding proteins include, but are not limited to, glucose/galactose-binding protein, maltose-binding protein, allose-binding protein, arabinose-binding protein, dipeptide-binding protein, glutamic acid/aspartic acid-binding protein, glutamine-binding protein, Fe(III)-binding protein, histidine-binding protein, leucine-binding protein, leucine/isoleucine/valine-binding protein, lysine/arginine/ ornithine-binding protein, molybdate-binding protein, oligopeptide-binding protein, phosphate-binding protein, ribose-binding protein, sulfate-binding protein, Zn(II)-binding protein, and vitamin B-12-binding protein.

The term "glucose/galactose binding protein" or "GGBP" or "maltose binding protein" or "MBP" as used herein refers to a type of protein naturally found in the periplasmic compartment of bacteria. These periplasmic proteins are naturally involved in chemotaxis and transport of small molecules (e.g., sugars, amino acids, and small peptides) into the cytoplasm. For example, GGBP is a single chain protein consisting of two globular α/β domains that are connected by three strands to form a hinge. The binding site is located in the cleft between the two domains. When glucose enters the binding site, GGBP undergoes a conformational change, centered at the hinge, which brings the two domains together and entraps glucose in the binding site. The wild type E. coli GGBP DNA and amino acid sequence can be found at www.ncbi.nlm.nih.gov/entrez/accession number D90885 (genomic clone) and accession number 23052 (amino acid sequence). In one embodiment, GGBP is from E. coli.

"Mutated binding protein" (for example "mutated GGBP") as used herein refers to binding proteins from bacteria wherein at least one amino acid has been substituted for, deleted from, or added to, the protein.

Mutations of binding proteins include for example, the addition or substitution of cysteine groups, non-naturally occurring amino acids, and replacement of substantially non-reactive amino acids with reactive amino acids.

Additional embodiments are mutations of the GGBP protein having a cysteine substituted for lysine at position 11 (K11C), a cysteine substituted for aspartic acid at position 14 (D14C), a cysteine substituted for valine at position 19 (V19C), a cysteine substituted for asparagine at position 43 (N43C), a cysteine substituted for glycine at position 74 (G74C), a cysteine substituted for tyrosine at position 107 (Y107C), a cysteine substituted for threonine at position 110 (T110C), a cysteine substituted for serine at position 112 (S112C), a double mutant including a cysteine substituted for serine at position 112 and serine substituted for leucine at position 238 (S112C/L238S), a cysteine substituted for lysine at position 113 (K113C), a cysteine substituted for lysine at position 137 (K137C), a cysteine substituted for glutamic acid at position 149 (E149C), a double mutant including a cysteine substituted for glutamic acid at position 149 and an arginine substituted for alanine at position 213 (E149C/A213R), a double mutant including a cysteine substituted for glutamic acid at position 149 and a serine substituted for leucine at position 238 (E149C/L238S), a double mutant including a serine substituted for alanine at position 213 and a cysteine substituted for histidine at position 152 (H152C/A213S), a cysteine substituted for methionine at position 182 (M182C), a cysteine substituted for alanine at position 213 (A213C), a double mutant including a cysteine substituted for alanine at position 213 and a cysteine substituted for leucine at position 238 (A213C/L238C), a cysteine substituted for methionine at position 216 (M216C), a cysteine substituted for aspartic acid at position 236 (D236C), a cysteine substituted for leucine at position 238 (L238C) a cysteine substituted for aspartic acid at position 287 (D287C), a cysteine substituted for arginine at position 292 (R292C), a cysteine substituted for valine at position 296 (V296C), a triple mutant including a cysteine substituted for glutamic acid at position 149 and a serine substituted for alanine at position 213 and a serine substituted for leucine at position 238 (E149C/A213S/L238S), a triple mutant including a cysteine substituted for glutamic acid at position 149 and an arginine substituted for alanine at position 213 and a serine substituted for leucine at position 238 (E149C/A213R/L238S), a cysteine substituted for glutamic acid at position 149 and a cysteine substituted for alanine at position 213 and a serine substituted for leucine at position 238 (E149C/A213C/L238S). Additional embodiments include mutations of GGBP at Y10C, N15C, Q26C, E93C, H152C, M182C, W183C, L255C, D257C, P294C, and V296C.

Additional embodiments are mutations of the maltose binding protein including, for example, D95C, F92C, I329C, S233C, and S337C.

Additional embodiments are histidine binding protein including, for example, E167C, K229C, V163C, Y230C, F231C, and Y88C.

Additional embodiments are mutations of the sulfate-binding protein including, for example, L65C, N70C, Q294C, R134C, W290C, and Y67C.

Additional embodiments are arabinose-binding protein including, for example, D275C, F23C, K301C, L253C, and L298C.

Additional embodiments are mutations of the dipeptide-binding protein including, for example, D450C, K394C, R141C, S111C, T44C, and W315C.

Additional embodiments are mutations of the glutamic acid/aspartic acid-binding protein including, for example, A207C, A210C, E119C, F126C, F131C, F270C, G211C, K268C, Q123C, and T129C.

Additional embodiments are mutations of the glutamine-binding protein including, for example, N160C, F221C, K219C, L162C, W220C, Y163C, and Y86C.

Additional embodiments are mutations of the Fe(III)-binding protein including, for example, E203C, K202C, K85C, and V287C.

Additional embodiments are mutations of the ribose-binding protein including, for example, T135C, D165C, E192C, A234C, L236C, and L265C.

Additional embodiments are mutations of the phosphate-binding protein including, for example, A225C, N223C, N226C, S164C, S39C, and A197C.

The mutation may serve one or more of several purposes. For example, a naturally occurring protein may be mutated in order to change the long-term stability of the protein, to conjugate the protein to a particular encapsulation matrix or polymer, to provide binding sites for detectable reporter groups, to adjust its binding constant with respect to a particular analyte, or combinations thereof. Long-term stability is intended to include thermal stability.

In one embodiment, analyte and mutated protein act as binding partners. The term "associates" or "binds" as used herein refers to binding partners having a relative binding constant (Kd) sufficiently strong to allow detection of binding to the protein by a detection means. The Kd may be calculated as the concentration of free analyte at which half the protein is bound, or vice versa. When the analyte of interest is glucose, the Kd values for the binding partners are between about 0.0001 mM and about 50 mM.

The fluorescent label can be attached to the mutated protein, for example a GGBP, by any conventional means known in the art. For example, the reporter group may be attached via amines or carboxyl residues on the protein. Exemplary embodiments include covalent coupling via thiol groups on cysteine residues of the mutated or native protein. For example, for mutated GGBP, cysteines may be located at position 10, at position 11, position 14, at position 15, position 19, at position 26, at position 43, at position 74, at position 92, at position 93, position 107, position 110, position 112, at position 113, at position 137, at position 149, at position 152, at position 154, at position 182, at position 183, at position 186, at position 211, at position 213, at position 216, at position 238, at position 240, at position 242, at position 255, at position 257, at position 287, at position 292, at position 294, and at position 296.

Any thiol-reactive group known in the art may be used for attaching reporter groups such as fluorophores to the cysteine in a natural or an engineered or mutated protein. For example, iodoacetamide, bromoacetamide, or maleimide are well known thiol-reactive moieties that may be used for this purpose.

Fluorophores that operate at long emission wavelengths (for example, about 575 nm or greater) are embodiments when the molecular sensor is to be used in vivo, for example, incorporated into an implantable biosensor device (the skin being opaque below about 575 nm). Conjugates containing these fluorophores, for example, attached at various cysteine mutants constructed in mutated GGBPs, can be screened to identify which ones result in the largest change in fluorescence upon glucose binding.

The following examples demonstrate the various embodiments of the invention.

Example 1

In this example, the process of Scheme I was used to produce iodoester squaraine nucleus 1.

Intermediate 1c: A mixture of butanol (5 mL) and benzene (5 mL) was added to a flask containing N-(2-hydroxyethyl)-N-methylaniline 1a (332 mg, 2.2 mmol) and 4-(N,N-dimethylaminophenyl)-3-hydroxy-cyclobuten-1,2-dione 1b (434 mg, 2.0 mmol). The mixture was heated to reflux, and 5 g of 4 Å molecular sieves were added. After 1 h the mixture turned a light blue green. After 24 h the mixture was a dark green-blue suspension. The solvent was evaporated, and the residue was washed with ethyl acetate (25 mL). The remaining residue was washed with water, leaving a dark blue residue. This mixture was transferred to a soxhlet thimble and extracted overnight with methylene chloride. After evaporation the residue was washed with ethyl acetate and yielded N-(2-hydroxyethyl)-N,N',N'-trimethyl-bis(4-aminophenyl)-squaraine 1c as a dark blue solid (223 mg, 30%).

Compound 1: One drop of DMF was added to a solution of iodoacetic acid (224 mg, 1.2 mmol) in methylene chloride (5 mL), and the resulting solution was added dropwise over a 1 min period to oxalyl chloride (180 mg, 1.4 mmol). After vigorous bubbling subsided, the pale orange solution was stirred for 30 min at 25° C. The solvent was removed under vacuum (~14 mm Hg), and the dark orange residue was kept under vacuum for 15 min. This residue was dissolved in methylene chloride (5 mL) to provide a solution of iodoacetyl chloride. The hydroxyethyl squaraine 1c from the preceding synthesis (175 mg, 0.5 mmol) was suspended in methylene chloride (20 mL). N,N-diisopropylethylamine (154 mg, 1.2 mmol) and the previously prepared iodoacetyl chloride solution were added to the squaraine suspension in sequential portions. The resulting blue heterogeneous mixture was stirred at 25° C. for 2 h. The solvent was evaporated, and the resulting dark blue solid was washed six times with 10 mL of ethylacetate, six times with ethyl ether, and dried under vacuum. This provided 204 mg of the iodoacetyl ester 1 as a pale purplish-blue solid. Fluorescence spectrum (methanol): 643 nm excitation maximum, 669 nm emission maximum.

Example 2

In this example, iodoacetamide squaraine nucleus 2 was produced by the process in Scheme II. This example corresponds to Scheme II where R is $C_2H_5$.

Intermediate 2b: 2-methylbenzothiazole (1 mM) 2a and N-bromoethylphthalimide (1 mM) were heated in a round bottom flask at 100° C. for 24 h. The resultant solids were isolated by filtration and purified by continuous washing with chloroform to obtain the intermediate 2b.

$^1$H NMR (CD$_3$OD, TMS) δ ppm: 4.295 (t, CH$_2$, 2H); 4.871 (s, CH$_3$, 3H); 5.102 (t, CH$_2$, 2H); 7.733 and 8.148-8.279 (m, aromatic, 8H).

Mol. Wt calculated for $C_{18}H_{15}N_2O_2S$ is 323(M+), found 323 (FAB)

Intermediate 2c: Dibutyl squarate was reacted with 3-ethyl-2-methyl-benzothiazolium iodide (1:1 ratio) in ethanol at reflux. After 30 minutes refluxing, the reaction mixture was filtered while hot. An orange colored solid crystallized out of the filtrate while cooling, which was separated and re-suspended in ethanol and treated with 40% NaOH solution under reflux. After 30 minutes, the contents were cooled and acidified with 2 N HCl (pH adjusted to 4). The product was extracted with chloroform to give intermediate 2c.

$^1$H NMR (CDCl$_3$, TMS) δ ppm: 1.385 (t, CH$_3$, 3H); 1.456 (t, CH$_3$, 3H); 4.064 (q, CH$_2$, 2H); 4.794 (q, CH$_2$, 2H); 5.479 (s, CH, 1H); 7.026-7.518 (m, aromatic, 4H).

Mol. Wt calculated for $C_{14}H_{11}NO_3S$ is 273(M+), found 273 (FAB)

Intermediate 2d: Intermediate 2b and 2c were reacted in a solvent mixture containing 1:1 (v/v) toluene and n-butanol. The reaction mixture was subjected to azeotropic distillation, and the water formed during the reaction was removed using a Dean-Stark trap. After 6 h, the reaction mixture was allowed to cool to room temperature, and the blue product was filtered out. Further purification was carried out using flash column chromatography over silica gel using methanol and chloroform (1:4 ratio) as eluent to obtain dye 2d.

$^1$H NMR (CDCl$_3$, TMS) δ ppm: 1.439 (t, CH$_3$, 3H); 4.127 (t, CH$_2$, 2H); 4.181 (q, CH$_2$, 2H); 4.381 (t, CH$_2$, 2H); 5.924 (s, CH, 1H); 5.964 (s, CH, 1H); 7.070-7.823 (m, aromatic, 12H).

Mol. Wt calculated for $C_{32}H_{23}N_3O_4S_2$ is 577(M+), found 577 (FAB).

Intermediate 2e: The dye 2d was dissolved in anhydrous methylene chloride and was treated with hydrazine monohydrate at room temperature. The deprotected squaraine dye precipitated from the reaction mixture and was isolated by filtration, followed by repeated washing with methylene chloride.

$^1$H NMR (CD$_3$OD, TMS) δ ppm: 1.420 (t, CH$_3$, 3H); 3.780 (t, CH$_2$, 2H); 4.320 (q, CH$_2$, 2H); 4.520 (t, CH$_2$, 2H); 5.924 (s, CH, 1H); 5.964 (s, CH, 1H); 7.200-7.850 (m, aromatic, 8H).

Mol. Wt calculated for $C_{24}H_{21}N_3O_2S_2$ is 447(M+), found 447 (FAB)

Compound 2: The intermediate dye 2e was dissolved in anhydrous methylene chloride, and an equivalent amount of iodoacetic anhydride was added. The mixture was stirred for 3 h at room temperature, and the product was isolated by evaporation of the solvent to obtain the final dye 2. Purification was carried out by repeated precipitation from hexane/methylene chloride.

$^1$H NMR (CD$_3$OD, TMS) δ ppm: 1.420 (t, CH$_3$, 3H); 3.900 (s, CH$_2$, 2H); 4.300 (q, CH$_2$, 2H); 4.450 (t, CH$_2$, 2H); 4.480 (t, CH$_2$, 2H); 5.820 (s, CH, 1H); 5.980 (s, CH, 1H); 7.200-8.200 (m, aromatic, 8H).

Mol. Wt calculated for $C_{26}H_{22}IN_3O_3S_2$ is 615(M+), found 615 (FAB).

Figure 2:
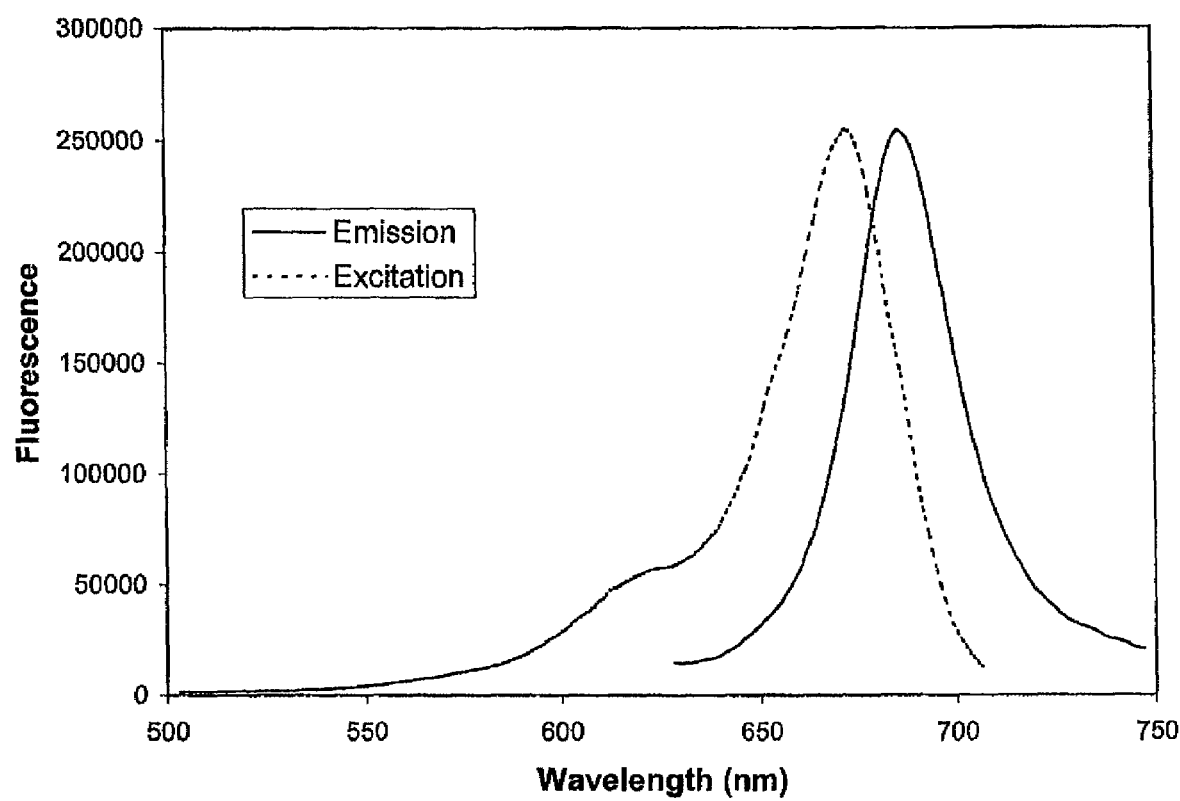
FIG. 2 is a graph showing the excitation and emission spectra of compound 2 in chloroform.

An illustrative absorbance spectrum is shown in FIG. 1 for compound 2 in chloroform. The excitation and emission spectra of compound 2 in chloroform are shown in FIG. 2.

Example 3

In this example, the process of Example 2 was repeated except for R being CH$_2$CH$_2$CO$_2$H of intermediate 3c in Scheme II. The resulting intermediate dye 3d with the protected amino group was characterized by NMR spectroscopy.

$^1$H NMR (DMSO-d$_6$, TMS) δ ppm: 2.720 (t, CH$_2$, 2H); 3.970 (t, CH$_2$, 2H); 4.470 (t, CH$_2$, 2H); 4.530 (t, CH$_2$, 2H); 5.760 (s, CH, 1H); 5.800 (s, CH, 1H); 7.100-8.450 (m, aromatic, 12H).

Compound 3: Deprotection of the amino group in 3d was carried out using methylamine in methanol by stirring a solution of the parent dye in methanol with 1 M methylamine in methanol. The product was isolated by evaporation of the solvent. The deprotected amine derivative 3e of the dye was reacted with iodoacetic anhydride (1:1) in methylene chloride, and the final product was isolated by filtration. The final dye 3 was purified by repeated precipitation using methylene chloride and hexane.

$^1$H NMR (DMSO-$d_6$, TMS) δ ppm: 1.420 (t, $CH_3$, 3H); 3.900 (s, $CH_2$, 2H); 4.300 (q, $CH_2$, 2H); 4.450 (t, $CH_2$, 2H); 4.480 (t, $CH_2$, 2H); 5.820 (s, CH, 1H); 5.980 (s, CH, 1H); 7.200-8.200 (m, aromatic, 8H).

Example 4

In this example, thiol-reactive Nile Red nulceus 4 was prepared according to Scheme III.

Intermediate 4b: N-phenyl-N-methyl-ethanolamine 4a (50 mmol) was suspended in conc. HCl (28 mL) and was cooled to 5° C. To this solution was added dropwise a sodium nitrite solution (6.67 g in 10 mL water) over a period of 40 min. After the addition, the reaction was kept stirring for 2 h more. The product was then filtered, washed with 0.5 M HCl, and dried in vacuo to give the nitroso compound 4b.

$^1$H NMR ($D_2O$) δ ppm: 3.59 (s, $CH_3$, 3H); 3.90 (t, $CH_2$, 2H); 4.05 (t, $CH_2$, 2H); 7.22-7.30 (m, aromatic, 2H); 7.50 (d, aromatic, 1H); 7.77 (d, aromatic, 1H). 13C NMR ($D_2O$) δ ppm: 42.44, 57.92, 58.72, 120.29, 122.52, 125.93, 140.56, 149.93, 163.21.

Mol. Wt calculated for $C_9H_{12}N_2O_2$ is 180(M+), found 181 (M+1) (FAB)

Intermediate 4d: 1,3-dihydroxynaphthalene 4c (5 mmol) was suspended in ethanol (25 mL) and was brought to reflux while stirring. To the refluxing solution was added intermediate 4b (5 mmol) in fractions over a period of 45 min. After the addition, the reaction mixture was maintained at reflux for 4 h more and was then cooled. The solvent was evaporated, and the product dye was purified by flash column chromatography over silica gel using methanol and chloroform (1:9) as eluent.

$^1$H NMR (CDCl$_3$) δ ppm: 2.98 (s, 3H), 3.48 (t, 2H), 3.83 (t, 2H), 6.20 (s, 1H), 6.77 (d, 1H), 7.10 (d, 1H), 7.45 (s, 1H), 7.60-7.75 (m, 3H), 7.72 (m, 1H), 8.08 (m, 1H). $^{13}$C NMR (CDCl$_3$) δ ppm: 39.2, 55.6, 60.3, 102.2, 110.2, 113.6, 124.7, 126.3, 126.6, 126.8, 130.6, 132.3, 133.7, 135.1, 145.8, 148.2, 152.4, 182.5, 183.8.

Mol. Wt calculated for $C_{19}H_{26}N_2O_3$ is 320(M+), found 321 (M+1) (FAB)

Compound 4: The intermediate dye 4d was dissolved in anhydrous acetonitrile (10 mL), and p-dimethylaminopyridine (3 mg) was added, followed by iodoacetic anhydride (250 mg). The reaction was stirred for 2 h. The product 4 was separated by evaporation of the solvent and then purified by repeated precipitation from methylene chloride and hexane.

$^1$H NMR (CDCl$_3$) δ ppm: 3.14 (s, 3H), 3.66 (s, 2H), 3.74 (t, 2H), 4.38 (t, 2H), 6.40 (s, 1H, ArH), 6.54 (d, 1H, ArH), 6.72 (d, 1H, ArH), 7.64-7.75 (m, 3H, ArH), 8.29 (d, 1H, ArH), 8.65 (d, 1H, ArH). $^{13}$C NMR (CDCl$_3$) δ ppm: −6.1, 39.6, 50.9, 63.0, 97.5, 106.4, 110.1, 124.1, 125.6, 126.0, 130.6, 131.2, 131.7, 131.98, 132.0, 141.5, 146.5, 151.8, 152.2, 169.0, 184.1.

Mol. Wt calculated for $C_{21}H17IN_2O_4$ is 488, found 489 (MH$^+$) (FAB-MS).

Example 5

This example produced Nile Red nucleus 5 according to the process of Scheme IV.

Intermediate 5b: 9-Diethylamino-2-hydroxy-5H-benz[a]phenoxazin-5-one 5a (50 mg, 0.15 mmol), N-bromoethylphthalimide (50 mg, 0.20 mmol) and potassium carbonate (60 mg, 0.09 mmol) were combined in DMF (15 mL) under argon with stirring. The reaction proceeded at reflux for 4.5 h. Additional bromoethylphthalimide (25 mg) was added at 4.5 h and at 6.5 h (15 mg). The temperature was lowered to 115° C., and the reaction proceeded overnight. DMF was removed in vacuo, and the residue was dried in vacuo. Column chromatography (2% MeOH/CH$_2$Cl$_2$) afforded 38 mg of the product 2-(2-phthalimidylethoxy)-Nile Red 5b.

$^1$H NMR (CDCl$_3$) δ ppm: 1.22 (t, 6H), 3.40 (q, 4H), 4.19 (t, 2H), 4.40 (t, 2H), 6.23 (s, 1H), 6.36 (d, 1H), 6.59 (dd, 1H), 7.09 (d, 1H), 7.52 (d, 1H), 7.70 (m, 2H), 7.84 (m, 2H), 7.96 (d, 1H), 8.13 (d, 1H). $^{13}$C NMR (CDCl$_3$) δ ppm: 12.8, 37.5, 45.2, 65.3, 96.3, 105.2, 106.5, 109.8, 118.6, 123.5, 124.9, 126.0, 127.9, 131.3, 132.1, 134.2, 139.6, 146.8, 150.7, 152.2, 161.0, 162.8, 168.4, 183.3. Mol. Wt calculated for $C_{30}H_{25}N_3O_5$ is 507, found 508 (MH$^+$) (FAB-MS).

Intermediate 5c: Intermediate 5b (30 mg, 0.06 mmol) was dissolved in anhydrous MeOH (8 mL) and was placed under argon. Next, methylamine (2M in MeOH, 4 mL, 8 mmol) was added. The reaction was carried out for 5 min at RT and 2.5 h at reflux. Flash chromatography was performed in 10% MeOH/CH$_2$Cl$_2$ to remove fast moving impurities and then at 30% MeOH/CH$_2$Cl$_2$ to elute the product 2-(2-aminoethoxy)-Nile Red 5c. Solvent was removed on a rotary evaporator, and the residue was dried in vacuo. Yield: 11 mg.

$^1$H NMR (CDCl$_3$) δ ppm: 1.25 (t, 6H), 3.17 (t, 2H), 3.45 (q, 4H), 4.20 (t, 2H), 6.27 (s, 1H), 6.43 (d, 1H), 6.63 (dd, 1H), 7.15 (m, 1H), 7.56 (d, 1H), 8.02 (m, 1H), 8.18 (d, 1H). $^{13}$C NMR (CDCl$_3$) δ ppm: 12.8, 41.6, 45.3, 63.9, 96.4, 105.4, 106.6, 109.9, 118.4, 124.9, 125.9, 127.4, 128.0, 131.3, 134.3, 147.1, 151.0, 152.3, 161.7, 183.5.

Mol. Wt calculated for $C_{22}H_{23}N_3O_3$ is 377, found 378 (MH$^+$) (FAB-MS).

Compound 5: Intermediate 5c (11 mg, 0.03 mmol) was dissolved in CH$_2$Cl$_2$ (5 mL). Iodoacetic anhydride (21 mg, 0.06 mmol) was then added and allowed to react for 40 min. An additional 25 mL of CH$_2$Cl$_2$ was added, and the reaction mixture was transferred to a separatory funnel. The organic phase was washed twice with 10% Na$_2$CO$_3$ (10 mL each), dried over anhydrous MgSO$_4$, and filtered. After the solvent was removed on a rotary evaporator, the final product 2-iodoacetylamidoethoxy-Nile Red nucleus 5 was dried under vacuum and precipitated from CH$_2$Cl$_2$/hexane. Yield: 3.4 mg.

$^1$H NMR (CDCl$_3$) δ ppm: 1.17 (t, 6H), 3.35 (q, 4H), 3.69 (t, 2H), 3.78 (s, 2H), 4.14 (t, 2H), 6.12 (s, 1H), 6.27 (s, 1H), 6.48 (dd, 1H), 6.91 (d, 1H), 7.34 (d, 1H), 7.74 (s, 1H), 7.95 (s, 1H). $^{13}$C NMR (CDCl$_3$) δ ppm: 12.9, 29.9, 40.1, 45.3, 66.9, 96.3, 105.2, 106.7, 109.8, 118.0, 124.9, 125.9, 127.8, 131.3, 134.1, 139.4, 147.0, 151.0, 152.2, 161.1, 168.1, 183.3.

Mol. Wt calculated for $C_{24}H_{24}IN_3O_4$ is 545, found 546 (M−H$^+$) (CI-MS).

Example 6

This example produces iodoacetamido benzodioxazole nucleus 6 according to Scheme V.

Intermediate 6b: Aminobenzodioxazole 6a (10 mmol) was reacted with ethyl bromide (50 mmol) in the presence of anhydrous potassium carbonate. The product was purified by column chromatography over silica gel using chloroform and methanol to afford the intermediate 6b in 65% yield.

Mol. Wt calculated for $C_{10}H_{13}N_3O$ is 191 (M+), found 191 (M+1) (FAB)

Intermediate 6c: POCl$_3$ (1 mL) was added to anhydrous DMF (4 mL) kept at ~5° C. in a round-bottomed flask with stirring. To this mixture was added intermediate 6b (0.4 g), and stirring continued for 1 h. The reaction was quenched by adding the reaction mixture to ice water (100 mL), followed by neutralization with 1N KOH (pH adjusted to ~9.0). The product was extracted with methylene chloride, and the organic phase was dried over sodium sulfate. The product was purified by column chromatography over silica gel using chloroform to afford 85% of the intermediate 6c.

$^1$H NMR (CDCl$_3$) δ ppm: 1.36 (t, CH$_3$, 6H); 3.91 (q, CH$_2$, 4H); 6.19 (d, CH, 1H); 7.82 (d, CH, 1H); 10.01 (s, CH, 1H).

Mol. Wt calculated for $C_{11}H_{13}N_3O_2$ is 219(M+), found 220 (M+1) (FAB)

Intermediate 6e: Intermediate 6c (350 mg) was reacted with intermediate 6d (644 mg, prepared in the same manner as intermediate 2b) in anhydrous methanol under reflux for 6 h in the presence of piperidine (50 mg) to form the parent dye 6e. The crystals that separated upon cooling were collected by filtration and then were purified by flash column chromatography over silica gel using a mixture of methanol (5%) and chloroform.

$^1$H NMR (CDCl$_3$, TMS) δ ppm: 1.42 (t, CH$_3$, 6H); 3.20 (t, 2H); 4.0 (q, CH$_2$, 4H); 4.40 (t, CH$_2$, 2H); 6.50 (s, CH, 1H); 6.51 (s, CH, 1H); 7.5-8.7 (m, aromatic, 10H).

Mol. Wt calculated for C$_{29}$H$_{26}$N$_5$O$_3$S is 524(M+), found 524 (FAB)

The obtained dye 6e showed a polar sensitivity as in Table 1 below:

TABLE 1

| Solvent | Relative Fluorescence |
|---|---|
| Methylene Chloride | 100 |
| Acetonitrile | 62 |
| Ethanol | 66 |
| Methanol | 50 |
| Water | 1 |

Such solvent polarity sensitivity of a dye is indicative of its environmental-sensitivity when attached to protein.

The parent intermediate benzodioxazole nucleus 6e can be deprotected using Na$_2$S and water to produce dye 6f and subsequently reacted with iodoacetic anhydride to form the target dye 6.

Example 7

This example produces iodoacetamido benzodioxazole nucleus 7 according to Scheme VI. Intermediate 7c was produced in the same manner as 6c from Example 6.

Intermediate 7d: 4-picoline (1 g) was reacted with 2-bromoethyl phthalimide (2.5 g) by heating at 125° C. for 12 h. The colorless solid formed was purified by repeated washing with chloroform to yield 3 g (86%) of the compound 7d.

$^1$H NMR (CD$_3$OD) δ ppm: 2.67 (s, CH$_3$, 3H); 4.30 (t, CH$_2$, 2H); 4.88 (t, CH$_2$, 2H); 7.81 (m, 4H); 7.93 (d, 2H); 8.93 (m 2H). $^{13}$C NMR (CD$_3$OD) δ ppm: 22.12, 39.63, 60.69, 124.49, 130.00, 132.90, 135.76, 145.45, 162.06, 169.20.

Intermediate 7e: Intermediate 7c (220 mg) was reacted with intermediate 7d (347 mg) in anhydrous methanol under reflux for 6 h in the presence of piperidine (50 mg) to form the parent dye 7e. The crude product was subjected to column chromatography over silica gel using methanol and chloroform (1:9) to obtain 7e.

Compound 7: Deprotection of the phthalimide in 7e provides intermediate 7f, which is then reacted with iodoacetic anhydride to produce the final product, compound 7.

Example 7-1

This example can be used to produce the iodoacetyl benzodioxazole nucleus 7' according to reaction Scheme VIa.

Compound 7a' is reacted with an equivalent amount of methyl iodide in presence of potassium carbonate and a phase transfer catalyst to form intermediate 7b'. A subsequent reaction of intermedicate 7b' with 2-bromoethanol produces intermediate 7c'. Vilsmaeir reaction on intermediate 7c' produces intermediate 7d', and a reaction of 7d' with 7e' produces intermediate 7f. A reaction of 7f with iodoacetic anhydride will produce the final compound 7'.

Example 8

This example produces the iodoacetyl benzodioxazole nucleus 8 according to Scheme VII.

Intermediate 8b: Aminobenzodioxazole 8a (10 mmol) was reacted with ethyl bromide (50 mmol) in the presence of anhydrous potassium carbonate. The product was purified by column chromatography over silica gel using chloroform and methanol to afford the intermediate 8b in 65% yield.

Mol. Wt calculated for C$_{10}$H$_{13}$N$_3$O is 191 (M+), found 191 (M+1) (FAB)

Intermediate 8c: POCl$_3$ (1 mL) was added to anhydrous DMF (4 mL) kept at ~5° C. in a round-bottomed flask with stirring. To this mixture was added intermediate 8b (0.4 g), and stirring continued for 1 h. The reaction was quenched by adding the reaction mixture to ice water (100 mL), and was followed by neutralization with 1N KOH (pH adjusted to ~9.0). The product was extracted with methylene chloride, and the organic phase was dried over sodium sulfate. The product was purified by column chromatography over silica gel using chloroform to afford 85% of the intermediate 8c.

$^1$H NMR (CDCl$_3$) δ ppm: 1.36 (t, CH$_3$, 6H); 3.91 (q, CH$_2$, 4H); 6.19 (d, CH, 1H); 7.82 (d, CH, 1H); 10.01 (s, CH, 1H).

Mol. Wt calculated for C$_{11}$H$_{13}$N$_3$O$_2$ is 219(M+), found 220 (M+1) (FAB-MS).

Intermediate 8d: A mixture of 2-methylbenzothiazole (2.24 g, 15 mmol) and 2-bromoethanol (2.90 g, 23 mmol) was taken in 25 mL flask. The reaction mixture was heated at 120° C. for 24 h. After 24 h the reaction mixture was cooled to room temperature and chloroform (20 mL) was added and stirred for 4 h at room temperature. The solid product was filtered, washed with chloroform and dried to give the desired product 8d as light brown solid. $^1$H NMR (CD$_3$OD) δ ppm: 3.26 (s, 3H), 4.06 (t, 2H), 4.94 (t, 2 H), 7.82 (t, 1H), 7.90 (t, 1H), 8.25-8.32 (m, 2H). $^{13}$C NMR (CD$_3$OD) δ ppm: 16.8, 52.3, 59.1, 117.0, 124.2, 128.5, 129.4, 129.7, 141.6, 178.1.

Intermediate 8e: Intermediate 8c (55 mg) was reacted with intermediate 8d (70 mg) in anhydrous methanol under reflux for 5 h in the presence of piperidine (100 mg) to form the parent dye 8e. The crystals that separated upon cooling were collected by filtration and confirmed by NMR and mass spectroscopy. $^1$H NMR (CD$_3$OD) δ ppm: 1.38 (t, 6H), 3.13 (t, 2H), 4.03 (q, 4H), 4.13 (t, 2H), 6.51 (d, 1H), 6.53 (d, 1H), 7.67 (m, 1H), 7.78 (m, 1H), 7.89 (m, 1H), 8.03 (m, 1H), 8.14 (m, 1H), 8.20 (m, 1H). $^{13}$C NMR (CD$_3$OD) δ ppm: 11.62, 44.54, 51.08, 59.18, 104.72, 108.01, 109.18, 115.96, 123.33, 127.47, 127.70, 129.09, 142.10, 143.40, 144.25, 144.97, 145.35, 149.04, 172.69.

Mol. Wt calculated for C$_{29}$H$_{26}$N$_5$O$_3$S is 395(M+), found 395 (FAB MS).

Compound 8: The parent dye 8e (20 mg) was reacted with iodoacetic anhydride (20 mg) by stirring at room temperature (3 h) in anhydrous methylene chloride (5 mL) in presence of pyridine (50 mg). The obtained product dye 8 was purified by precipitation from hexane.

Mol. Wt calculated for C$_{23}$H$_{24}$IN$_4$O$_3$S$^+$ is 563 (M+), found 563 (FAB)

Example 8-1

This example produces the iodoacetyl benzodioxazole nucleus 8' according to reaction scheme VIIa.

Compound 8a' is reacted with an equivalent amount of methyl iodide in the presence of anhydrous potassium carbonate and a phase transfer catalyst to form the mono-methylamino derivative 8b'. Compound 8b' is then reacted with 2-bromoethanol in presence of potassium carbonate and phase transfer catalyst to form intermediate 8c'. Vilsmaeir reaction on 8c' produces intermediate 8d', which is reacted with 8e' to form intermediate 8f. A subsequent reaction of intermediate 8f with iodoacetic anhydride produces the final compound 8'.

Example 9

This example produces the aza coumarin nucleus 9 according to scheme VIII.

Intermediate 9b. A solution of N,N'-dimethylamino phenol 9a (3.42 g, 25 mmol) in 10 mL of concentrated HCl was placed in a 100 mL flask and the mixture was cooled to 5° C. The content in the flask was stirred vigorously and a solution of NaNO$_2$ (1.80 g, 26 mmol) in water (5 mL) was added directly into the reaction mixture over a period of 30 min. The reaction temperature was maintained at 5° C. throughout the period of addition. After the addition was over, the reaction mixture was stirred for 1 h at 5° C. and filtered. The solids were washed with 10 mL of 5M HCl followed by ethanol (25 mL) and dried in air to give a yellow solid 9b (3.00 g, 72%).

Mol. Wt calculated for C$_8$H$_{10}$N$_2$O$_2$ is 166.18, found 167 (MH$^+$) (FAB-MS).

Intermediate 9e. A slurry of 10% Pd/C (25 mg) in 5 mL of methanol was stirred for 15 min. under an atmosphere of argon. A solution of NaBH$_4$ (190 mg, 5.0 mmol) in methanol (5 mL) was added to this slurry. A solution of the nitroso compound 9b (500 mg, 2.5 mmol) dissolved in methanol (13 mL) and containing triethylamine (2 mL) was added dropwise to the Pd/C slurry over a period of 5 min. The red nitroso compound turned into light yellow during the reduction reaction. After 15 min, an additional amount of NaBH$_4$ (190 mg, 5 mmol) in methanol (4.0 mL) was added to ensure complete reduction to form intermediate 9c. Stirring was continued for another 30 min, ethylpyruvate 9d (3.0 mL, 27 mmol) was added to the reaction mixture, and then the contents were heated to reflux. After 3 h of refluxing, the reaction mixture was cooled to room temperature and filtered through celite to remove the unreacted Pd/C. The filtrate was evaporated to obtain a residue, which was chromatographed over silica gel and eluted with a mixture of hexane and ethyl acetate (9:1 v/v), to give a yellow solid 9e (400 mg, 78%). $^1$H NMR (CDCl$_3$) δ ppm: 2.48 (s, 3H), 3.06 (s, 6H), 6.40 (s, 1H), 6.65 (m, 1H), 7.50 (m, 1H). $^{13}$C NMR (CDCl$_3$) δ ppm: 21.0, 40.5, 97.5, 109.8, 122.9, 129.2, 147.6, 148.9, 152.0, 154.7.

Mol. Wt calculated for C$_{11}$H$_{12}$N$_2$O$_2$ is 204, found 205 (MH$^+$) (FAB-MS).

Intermediate 9g. POCl$_3$ (1.13 g, 7.4 mmol) was added to anhydrous DMF (15 mL) kept at 5° C. The mixture was stirred under an atmosphere of argon for 30 min. at 5° C. and then 2-(methylphenylamino)-ethanol (1.12 g, 7.4 mmol) 9f was added and the resulting solution was stirred at room temperature for 3 h. The reaction mixture was hydrolyzed by slow addition of ice-cold water and neutralized by the addition of NaOH (2 M) and the pH was adjusted to 7.0. The product was extracted with methyl tert-butyl ether (3×50 mL), dried over anhydrous Na$_2$SO$_4$ and evaporated to give a yellow liquid. The product was purified by column chromatography as follows. The crude product was chromatographed over silica gel and eluted with a mixture of hexane and ethyl acetate, (9:1 v/v). Evaporation of the pure fractions yielded compound 9g (0.80 g, 60%). $^1$H NMR (CDCl$_3$) δ ppm: 3.00 (s, 3H), 3.64 (t, 2H), 4.36 (t, 2H), 6.76 (m, 2H), 7.28 (m, 2H), 8.07 (s, 1H). $^{13}$C NMR (CDCl$_3$) δ ppm: 38.9, 51.2, 61.3, 112.4, 117.1, 129.5, 149.0, 161.2.

Mol. Wt calculated for C$_{10}$H$_{13}$NO$_2$ is 179, found 179 (M+) (FAB-MS).

Intermediate 9h. A solution of compound 9e (100 mg, 0.49 mmol) and compound 9g (100 mg, 0.56 mmol) in anhydrous methanol (4 mL) was stirred under an atmosphere of argon. To this solution, sodium methoxide (26 mg, 0.50 mmol) was added and the reaction mixture was heated to reflux. After 4 h, the reaction mixture was cooled to room temperature and evaporated to afford a dark brown residue. The obtained residue was dissolved in minimum amount of chloroform and chromatographed over silica gel. Elution with a mixture of methanol and chloroform (5:95, v/v) yielded the product 9h as a solid (40 mg, 23%). $^1$H NMR (CDCl$_3$) δ ppm: 2.96 (s, 6H), 3.10 (s, 3H), 3.47 (t, 2H), 3.82 (t, 2H), 6.36 (s, 1H), 6.46 (s, 1H), 6.53 (d, 1H), 6.75 (m, 1H), 6.80 (d, 2H), 7.24 (m, 2H), 7.56 (d, 1H). $^{13}$C (CDCl$_3$) δ ppm: 38.9, 40.6, 55.7, 60.3, 96.9, 102.2, 103.8, 111.0, 113.3, 117.4, 129.4, 129.8, 143.1, 144.5, 145.3, 149.7, 150.3, 151.8, 178.88.

Compound 9 (Iodoacetylaza-coumarin, IAZCO). To a solution of compound 9h (20 mg, 0.060 mmol) in anhydrous chloroform (2 mL), pyridine (50 µL) was added and stirred under an atmosphere of argon for 5 min. To this solution was added iodoaceticanhydride (30 mg, 0.09 mmol) and the stirring was continued for 2 h. Chloroform was evaporated off and the residue was chromatographed over silica gel and eluted with a mixture of methanol and chloroform (5:95, v/v) to give the product 9 as a dark solid. (25 mg, 85%).

Example 9-1

This example produces the azacoumarin nucleus 9' according to the reaction scheme VIIIa.

3-hydroxy-N-methylaniline 9a' is reacted with sodium nitrite in presence of HCl to produce the compound intermediate 9b'. Reduction of the nitroso group of 9b' is carried out with Pd/C and sodium borohydride to produce the intermediate 9c', followed by reaction with 9d' to produce intermediate 9e'. A reaction of 2-bromoethanol with intermediate 9e' produces intermediate 9f'. Intermediate 9f' is reacted with 9g' to produce intermediate 9h'. The final product 9' is obtained by reacting 9h' with iodoacetic anhydride in presence of pyridine.

Example 10

In this Example, reaction Scheme IX was used to produce the Compound 10.

Intermediate 10c. 4-(diethylamino)salicylaldehyde 10a (2.00 g, 10.0 mmol) and diethyl glutaconate 10b (2.00 g, 11.0 mmol) were refluxed in absolute ethanol (25 mL) in presence of piperidine (50 mg). After 6 h refluxing, the reaction mixture was cooled to room temperature and the yellow crystals obtained was separated, washed with cold ethanol (10 mL) and dried under vacuo to obtain the desired product 10c (2.60 g, 82%). $^1$H NMR (CDCl$_3$) δ ppm: 1.22 (t, 6H), 1.29 (t, 3H), 3.42 (q, 4H), 4.23 (q, 2H), 6.48 (d, 1H), 6.60 (d, 1H), 6.94 (d, 1H), 7.30 (d, 1H), 7.53 (d, 1H), 7.70 (s, 1H). $^{13}$C NMR (CDCl$_3$) δ ppm: 12.7, 14.6, 45.2, 60.6, 97.2, 108.8, 109.6, 114.8, 119.7, 130.0, 139.6, 144.6, 151.9, 156.7, 160.5, 168.0.

Mol. Wt calculated for C$_{18}$H$_{21}$NO$_4$ is 315, found 315 (M$^+$) (FAB-MS).

Intermediate 10d. Water (3 mL) was added to a solution of compound 10c (1.00 g, 0.315 mmol) in THF (12 mL). To this mixture, 20 mg of OsO$_4$ (2.5% in t-butanol) was added and the obtained reaction mixture was stirred at room temperature for an hour. After this period, portions of powdered NaIO$_4$ (1.50 g, 7.0 mmol) were added over a period of 30 min and stirring continued for an additional 48 h. After stirring, the solvent was removed and the obtained solid was dissolved in CH$_2$Cl$_2$ (200 mL) and washed with water (75 mL). The organic layer was washed with brine, dried over sodium sulfate and evaporated to obtain a yellow solid. The crude product containing small amounts of starting material was purified by silica gel column chromatography (CH$_2$Cl$_2$/EtOAc, 4:1) to yield the pure product 10d as a yellow solid (320 mg, 41%). $^1$H NMR (CDCl$_3$) δ ppm: 1.25 (t, 6H), 3.48 (q, 4H), 6.48 (d, 1H), 6.64 (m, 1H), 7.40 (d, 1H), 8.25, (s, 1H), 10.12 (s, 1H). $^{13}$C NMR (CDCl$_3$) δ ppm: 12.67, 45.49, 97.35, 108.43, 110.39, 114.50, 132.4, 145.6, 153.7, 159.2, 162.1, 188.2.

Mol. Wt calculated for C$_{14}$H$_{15}$NO$_3$ is 245, found 246 (MH$^+$) (FAB-MS).

Intermediate 10f. A mixture of 2-methylbenzothiazole 10e (2.24 g, 15 mmol) and 2-bromoethanol (2.90 g, 23 mmol) was taken in 25 mL flask. The reaction mixture was heated at 120° C. for 24 h. After 24 h the reaction mixture was cooled to room temperature, and chloroform (20 mL) was added and stirred for 4 h at room temperature. The solid product was filtered, washed with chloroform and dried to give the desired product 10f as light brown solid. $^1$H NMR (CD$_3$OD) δ ppm: 3.26 (s, 3H), 4.06 (t, 2H), 4.94 (t, 2H), 7.82 (t, 1H), 7.90 (t, 1H), 8.25-8.32 (m, 2H). $^{13}$C NMR (CD$_3$OD) δ ppm: 16.8, 52.3, 59.1, 117.0, 124.2, 128.5, 129.4, 129.7, 141.6, 178.1.

Intermediate 10g. A solution of coumarin aldehyde 10d (60 mg, 0.22 mmol) and compound 10f (50 mg, 0.20 mmol) in anhydrous methanol (3 mL) was taken in a 10 mL flask. To this solution piperidine (30 mg) was added and heated to reflux. The light brown reaction mixture slowly changed to violet in about 30 min. The contents were refluxed overnight, cooled to room temperature and purified by column chromatograpy over silica gel using chloroform containing 3% methanol as the solvent. Evaporation of the pure fractions yielded 45 mg of the desired dye, 10g.

Compound 10 (ICOBzT). To a solution of compound 10g (30 mg, 0.060 mmol) in anhydrous chloroform (3 mL), was added pyridine (30 mg) and stirred under an atmosphere of argon. Iodoacetic anhydride (30 mg, 0.080 mmol) was added to this stirred reaction mixture and continued the stirring for 3 h. The solvent was then evaporated and the obtained residue was chromatographed over silica gel. Elution with chloroform containing 5% methanol yielded the pure compound 10 as a purple solid. Glucose/galactose mutant A213C conjugated to 10 (ICOBzT) as described herein, showed a wavelength shift of 10 nm (red shift) in presence of 100 mM of glucose. (shifted from 622 to 632 nm).

Example 10-1

This example produces the coumarin nucleus 10' according to reaction scheme IXa.

3-hydroxy-N-ethylaniline (10a') is reacted with 2-bromoethanol to produce intermediate 10b'. Vilsmaeir reaction is carried out on 10b' to obtain intermediate 10c'. Further reaction of 10c' with 10d' produces intermediate 10e'. Reaction with OsO$_4$ and sodium periodate produces intermediate 10f'. Subsequently, 10f' is reacted with 10g' to produce intermediate 10h'. The desired product 10' is obtained by the reaction of 10h' with iodoacetic anhydride.

Example 11

Figure 3:
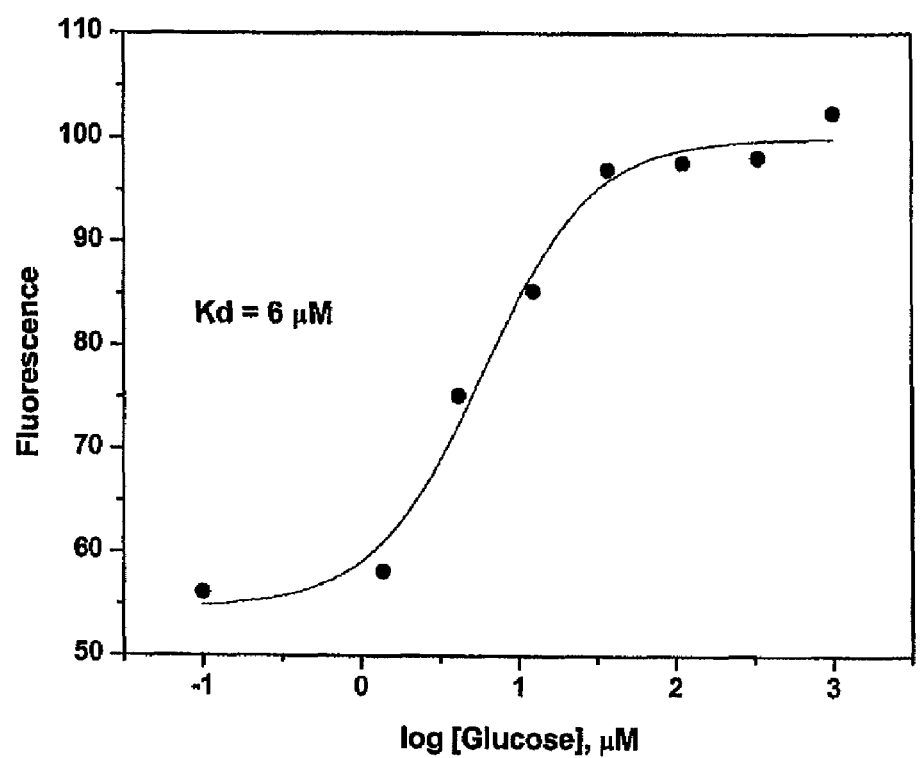
FIG. 3 is a titration curve of compound 1 conjugated to H152C GGBP in PBS buffer.

GGBP Conjugation. A solution of H152C GGBP (4 nmol) in 200 uL PBS buffer was prepared, and this was incubated with DTT (8 nmol) for 30 minutes at room temperature. A solution of the squaraine iodoester nucleus 1 (1 mg, partially dissolved in 120 uL DMSO) was added, and the mixture was wrapped in foil and left for 4 h at room temperature. The labeled protein was obtained as the second fraction from a NAP-5 size exclusion column, eluting with PBS buffer. The protein was assayed for its fluorescence response to glucose in several wells of a 96 well microwell plate with glucose added in PBS giving final glucose concentrations between 0 and 1 mM. The fluorescence response of the labeled protein to glucose was determined by adding glucose to a solution of the labeled protein in PBS buffer. Typically the fluorescence measurements employed either a Varian Cary Eclipse fluorimeter (Varian, Inc., Palo Alto, Calif.) or a PTI spectrofluorimeter (Photon Technology International, Inc., Lawrenceville, N.J.). The plate fluorescence was read using a Varian Cary Eclipse fluorometer equipped with a microwell plate adapter using excitation at 625 nm and emission at 660 nm. Thus, the squaraine iodoester nucleus 1-binding protein conjugate fluorescence property corresponded to analyte concentration and therefore functioned as a biosensor. This indicated an approximate Kd of 6 uM between the labeled protein and glucose as shown in FIG. 3.

Further labeling of individual GGBP variants was performed with the squaraine iodoester 1. Binding constants (Table 2) were determined by preparing samples with approximately 0.1 μM labeled protein in buffer (PBS) in a 96 well microplate and adding solutions of varying concentrations of glucose (giving final concentrations between 0 and 1 mM or between 0 and 10 mM). The K$_d$ was determined from the following relationships as adapted from M. L. Pisarchick and N. L. Thompson "Binding of a monoclonal antibody and its Fab fragment to supported phospholipid monolayers measured by total internal reflection fluorescence microscopy" Biophys. J. 1990, 58, 1235-1249: where F is fluorescence intensity, F$_{inf}$ is fluorescence at infinity, F$_0$ is fluorescence at zero glucose, and x is the free concentration of glucose ([Glc]$_{free}$) as determined by the relationship:

$$[GLc]_{free} = \frac{[GLC]_{tot} - [Prot]_{tot} - Kd + \sqrt{([Glc]_{tot} - [Prot]_{tot} - Kd)^2 + 4*[Glc]_{tot}*Kd}}{2}$$

where [Glc]$_{tot}$ and [Pro]$_{tot}$ are the total concentrations of glucose and protein, respectively. Note that when [GLc]$_{tot}$>>Kd and [GLc]$_{tot}$>>[Pro]$_{tot}$, the above two equations may be simplified to the following form:

$$F = F_0 + [(F_{const}*x)/(1+x/Kd)]$$

where F$_{const}$=(F$_{inf}$-F$_0$)/K$_d$.

TABLE 2

| Mutant GGBP | Fluorescence Intensity Change (%) | Kd (mM) for Glucose |
|---|---|---|
| H152C GGBP | +100% | 0.006 |
| E149C/A213R GGBP | +100% | 0.068 |
| A213C/L238C GGBP | +130% | 0.75 |

Example 12

Several conjugates of dye 2 with GGBP (glucose/galactose binding protein) were prepared that had cysteine substitutions in the protein as identified in Table 3. In general, conjugates of compound 2 with GGBP were substantially more stable in solution than conjugates of compound 1 with GGBP. An aliquot of the protein in PBS buffer was treated with DTT (dithiothreitol) for 10-30 minutes followed by addition of the iodoacetyl squaraine dye in DMSO. After approximately 3-4 hours the reaction was stopped, and dye-labeled protein was obtained by size-exclusion chromatography (NAP-5 column). The fluorescence response was determined with excitation at 600 nm and emission scanned between 625 nm and 700 nm. Emission maxima were observed near 660 nm.

Figure 4:
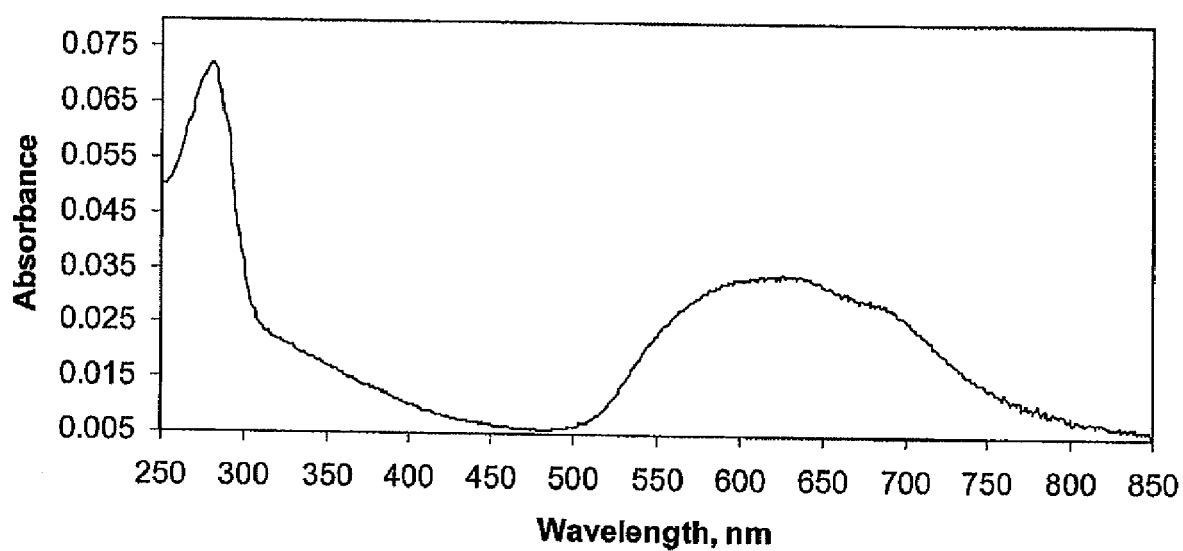
FIG. 4 is a graph showing the absorbance spectrum of compound 2 conjugated to V19C GGBP in PBS buffer.

The absorption spectrum for the conjugate of compound 2 with V19C GGBP is shown in the graph of FIG. 4. This absorption spectrum is typical for the conjugates described herein.

Figure 5:
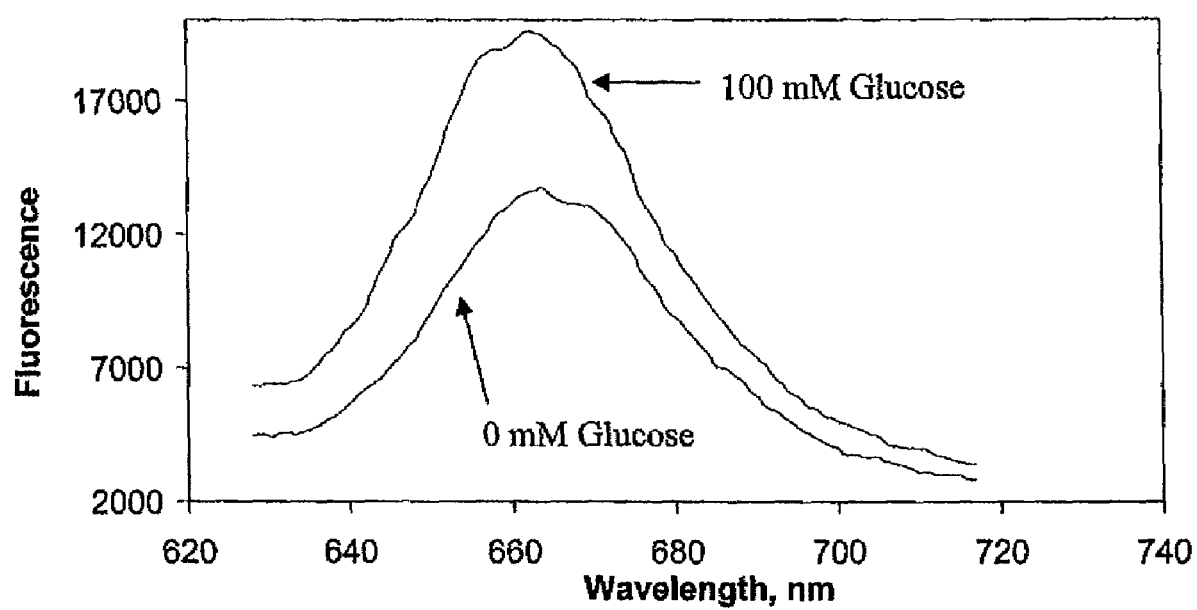
FIG. 5 is a graph showing the change in fluorescence of compound 2 conjugated to V19C GGBP in response to a change in glucose concentration in PBS buffer.

All the conjugates were treated with at least 10 mM of glucose, and the fluorescence changes were monitored. FIG. 5 illustrates the change in fluorescence observed with change in glucose concentration for compound 2 conjugated to V19C GGBP. For the derivative A213C, a 2-3 nm fluorescence shift to the blue region was observed upon glucose binding. Thus, the squaraine iodoester nucleus 2-binding protein conjugate fluorescence property corresponded to analyte concentration and therefore functioned as a biosensor.

TABLE 3

| GGBP Mutant | Fluorescence Intensity Change (%) |
| --- | --- |
| E149C/A213R/L238S | +5% |
| K11C | −5% |
| K113C | −15% |
| V19C | +25% |
| W183C | +17% |
| D236C | +15% |
| M182C | −14% |
| T110C | −15% |

Example 13

The same protocol was used to label E149C GGBP, H152C GGBP and S337C MBP with the Nile Red compounds 4 and 5. Fluorescence excitation was at 550 nm, and the emission maximum was 650 nm. The change in fluorescence intensity is shown in Table 4. Thus, the Nile Red nucleus 4- and 5-binding protein conjugate fluorescence property corresponded to analyte concentration and therefore functioned as a biosensor.

TABLE 4

| Nile Red-Binding Protein Conjugate | Fluorescence Intensity change (%) |
| --- | --- |
| E149C GGBP with compound 5 | +9% |
| H152C GGBP with compound 5 | +6% |
| S337C MBP with compound 4 | +200% |

Example 14

Glucose/Maltose sensing using 9 (IAZCO). The aza-coumarin nucleus IAZCO was conjugated to glucose binding protein (GBP) and maltose binding protein (MBP) as described in the previous examples. Derivatives of the protein GGBP (glucose/galactose binding protein) and MBP (maltose binding protein) with cysteine residue substitutions were prepared. Typically, an aliquot of the protein in PBS buffer was treated with DTT (dithiothreitol) for 10-30 minutes followed by addition of the dye 9 in DMSO. After approximately 3-4 hours, the reaction was stopped and dye-labeled protein was obtained by size-exclusion chromatography (NAP-5 column). The fluorescence response of the labeled protein to glucose/maltose was determined by adding glucose/maltose with excitation at 600 nm and emission scanned between 620 nm and 700 nm. Thus, glucose/galactose binding protein mutant E149C conjugated to 9 (IAZCO) showed a wavelength shift of 9 nm (blue shift) in presence of 100 mM glucose (shifted from 653 nm to 644nm) and thus functioned as a biosensor.

The fluorescence changes observed for 9 with different proteins and glucose/maltose are given in Table 5. These results were obtained by measuring the fluorescence of the dye-protein conjugate (<1.0 μM) in PBS (at pH 7.4). Saturation amounts (100 mM) of glucose/maltose were added, and the ratio of the fluorescence was obtained. Thus, the aza-coumarin nucleus 9-binding protein conjugate fluorescence property corresponded to analyte concentration and therefore functioned as a biosensor.

TABLE 5

| GGBP/MBP Mutant | Change in Fluorescence Intensity | Conc. of glucose/Maltose | Kd (mM) |
| --- | --- | --- | --- |
| E149C GGBP | +60% | 100 mM | -na |
| A213C GGBP | +130% | 100 mM | 0.013 |
| H152C GGBP | +75% | 100 mM | -na |
| V19C GGBP | −50% | 100 mM | -na |
| E149C, A213C, L238S GGBP | +100% | 100 mM | 30 |
| S337C MBP | +1100% | 100 mM | 0.060 |

Example 15

Reading Through Skin Experiment

In one embodiment, in vitro through skin glucose/maltose sensing experiments were performed using the herein described NIR dyes.

Three protein-NIR conjugates (shown below) were chosen as the test substrates.
- (a) A213C GGBP conjugated to iodoacetyl aza-coumarin nucleus (IAZCO) of Compound 9
- (b) S337C MBP conjugated to iodoacetyl aza-coumarin nucleus (IAZCO) of Compound 9
- (c) S337C MBP conjugated to iodoacetyl Nile red nucleus (INR) of Compound 4

These conjugates were infused into crosslinked polyethylene glycol (PEG) disks and the disks were used for read-through-skin studies. The PBS solutions of these conjugates in micro-well plates were also studied through skin. A blank PEG disk and PBS were used as the control. The activity of the proteins in PBS and PEG disks were tested prior to in vitro experiment.

(i) Response to Glucose

Figure 6:
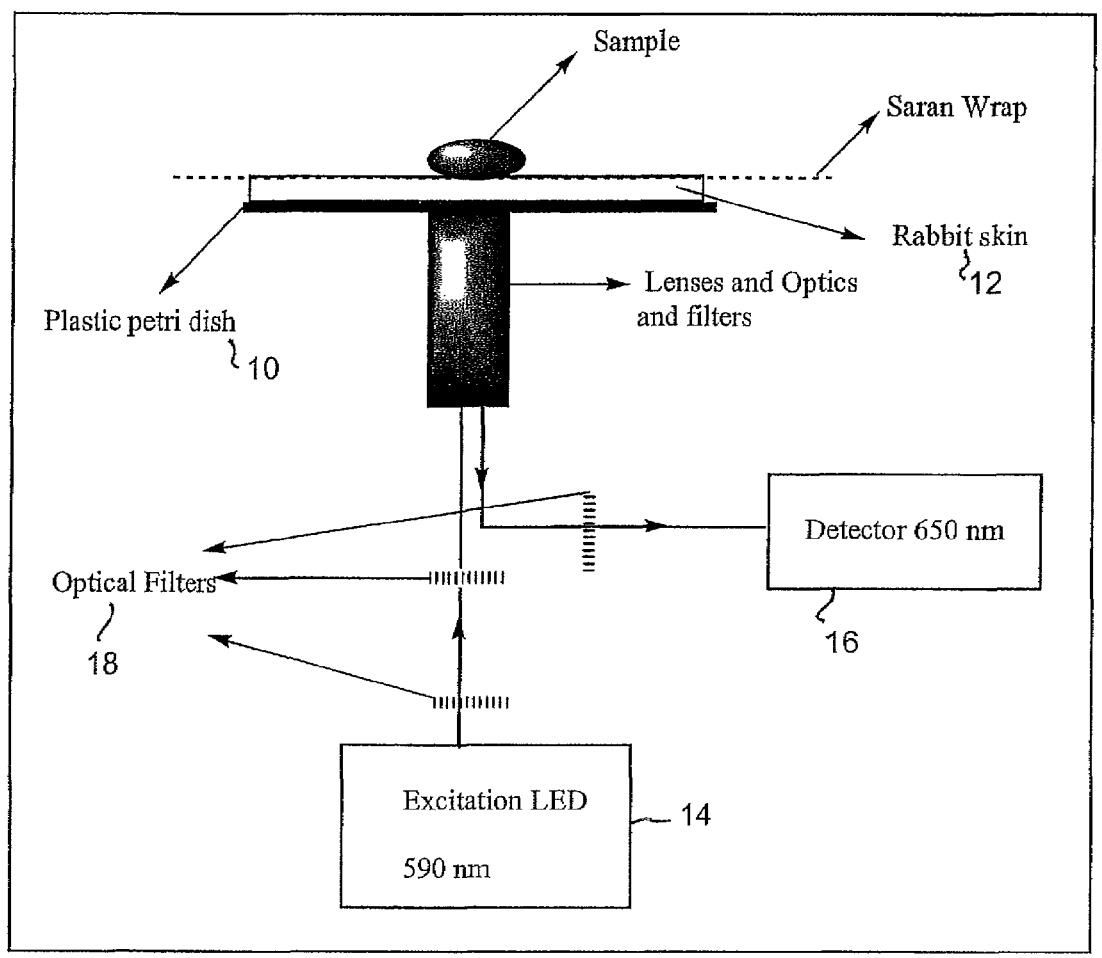
FIG. 6 is a schematic view of instrumentation used in Example 15.

Referring to FIG. 6, the PEG disks 10 were placed over a piece of rabbit skin 12 and was excited by a laser 14 and read from the other side of the skin by a detector 16.The Rabbit skin was about 3-4 mm thick and was not transparent to human eye. Excitation was carried out using 590 nm LED light and the fluorescence was monitored at 650 nm. Filters 18 were used to avoid interference from the excitation light and scattering.

Figure 7:
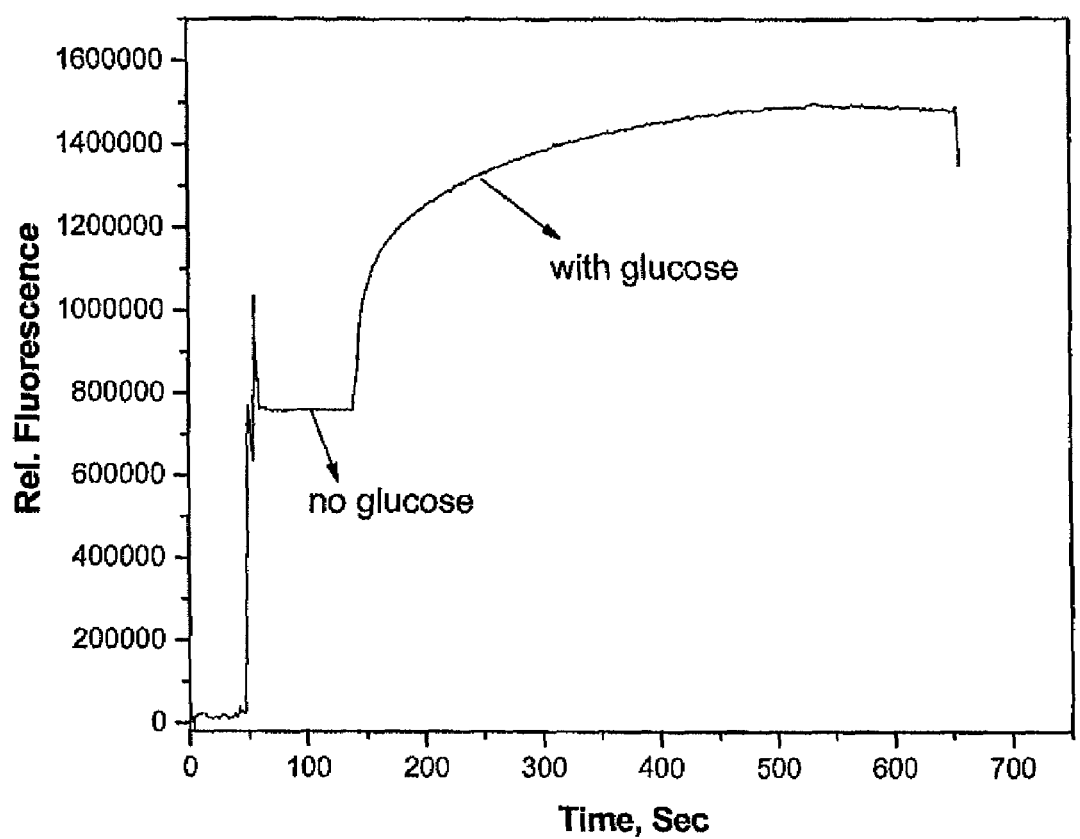
FIG. 7 illustrates a change in a fluorescence property of 9 conjugated to A213C GGBP upon addition of glucose in an in vitro through skin measurement.

The fluorescence was stable for both PEG disks and solutions, and upon addition of glucose the fluorescence intensity rose and kept increasing for 2-4 minutes. This time lag may represent a slow diffusion of glucose/maltose in to the hydrogel as shown in FIG. 7. For the solution control, the response was fast and no lag was noticed. Control studies using blank PEG disk and PBS solutions showed no change in fluorescence upon addition of glucose. Thus, the aza-coumarin nucleus 9-binding protein conjugate, and Nile Red nucleus 4-binding protein conjugate fluorescence property corresponded to the presence of analyte and therefore functioned as a through-skin biosensor.

(ii): Response to Maltose using MBP

The above experiments were repeated using the INR-MBP PEG disks and solutions. As in the case of A213C GGBP conjugated to 9, the fluorescence was stable for both PEG disks and solutions. The fluorescence intensity rose and kept increasing for 2-4 minutes upon addition of maltose.

The following Table 6 summarizes the change in fluorescence intensity observed for the read-through-skin experiment.

TABLE 6

| Substrate | Solution Change in Fluorescence Intensity | Change in Fluorescence Intensity of PEG disks Through-skin | Change in Fluorescence Intensity of solution Through-skin |
|---|---|---|---|
| A213C-IAZCO GGBP | +120% | +96% | +96% |
| S337C-IAZCO MBP | +372% | +42% | +500% |
| S337C-INR MBP | +213% | +111% | +270% |

The data provided in these examples demonstrate that the dyes and the conjugates exhibit analyte binding and stability under ambient conditions. While several embodiments have been selected to demonstrate the various embodiments of the invention, it will be understood by those skilled in the art that various changes and modifications can be made without departing from the scope of the invention as defined in the appended claims.

What is claimed is:

1. A compound having the formula

A-Y where A is a Nile Red nucleus having a formula selected from the group consisting of;

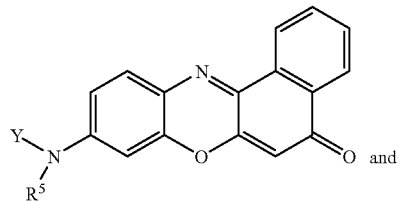 and

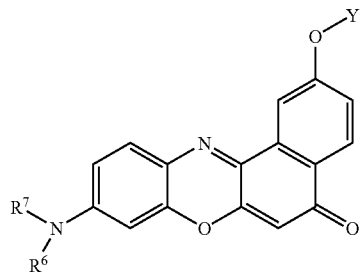

where $R^5$, $R^6$ and $R^7$ are independently methyl, ethyl, or propyl;

and where Y is

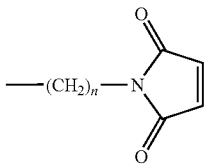

where n is an integer of 1 to 6;
A'—CO—$R^1$, where A' is —$R^2$O— or —$R^2$N($R^3$)—, where $R^2$ is a $C_1$ to $C_6$ alkyl, $R^3$ is H or $CH_3$, and $R^1$ is $CH_2Cl$, $CH_2Br$, $CH_2I$; or

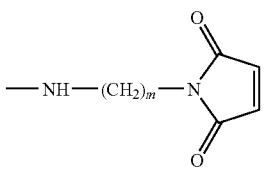

where m is an integer of 2 to 6.

2. The compound of claim 1, wherein $R^2$ is a $C_2$ to $C_4$ alkyl.
3. The compound of claim 2, wherein $R^2$ is $CH_2CH_2$.
4. The compound of claim 1, wherein $R^2O$ is —$CH_2CH_2O$—.
5. The compound of claim 1, wherein $R^2N(R^3)$— is —$CH_2CH_2NH$—.
6. The compound of claim 1, wherein said compound is

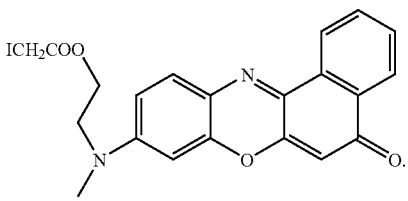

7. The compound of claim 1, wherein said compound is

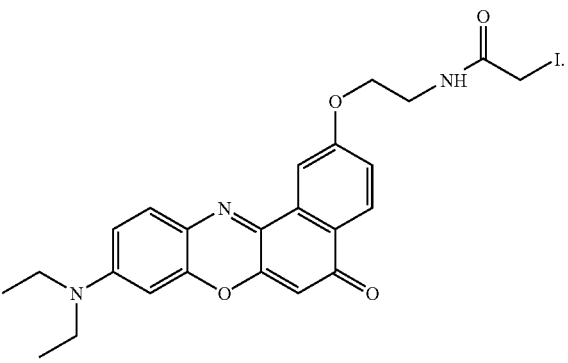

* * * * *